(12) United States Patent
Mizutani et al.

(10) Patent No.: US 8,328,781 B2
(45) Date of Patent: Dec. 11, 2012

(54) INTERLABIAL PAD AND PACKAGE THEREOF

(75) Inventors: Satoshi Mizutani, Kanonji (JP); Koichi Yamaki, Kanonji (JP); Yuki Noda, Kanonji (JP)

(73) Assignee: Uni-Charm Corporation, Kawanoe-shi (JP)

( * ) Notice: Subject to any disclaimer, the term of this patent is extended or adjusted under 35 U.S.C. 154(b) by 196 days.

(21) Appl. No.: 12/196,918

(22) Filed: Aug. 22, 2008

(65) Prior Publication Data
US 2009/0030394 A1  Jan. 29, 2009

Related U.S. Application Data

(60) Division of application No. 10/705,810, filed on Nov. 10, 2003, now abandoned, which is a continuation of application No. PCT/JP02/04897, filed on May 21, 2002.

(30) Foreign Application Priority Data

May 22, 2001 (JP) ................................. 2001-152403
Sep. 25, 2001 (JP) ................................. 2001-291101

(51) Int. Cl.
*A61F 13/15* (2006.01)
*A61F 13/20* (2006.01)
(52) U.S. Cl. ........ 604/385.01; 604/385.101; 604/385.17
(58) Field of Classification Search ............. 604/385.17–385.19, 904, 101, 604/385.01, 385.101
See application file for complete search history.

(56) References Cited

U.S. PATENT DOCUMENTS

| 3,183,909 A | 5/1965 | Roehr |
| 4,595,392 A | 6/1986 | Johnson et al. |
| D404,814 S | 1/1999 | Mayer |
| 5,868,727 A | 2/1999 | Barr et al. |

(Continued)

FOREIGN PATENT DOCUMENTS

CA    2277728    11/1999

(Continued)

OTHER PUBLICATIONS

Mizutani, et al., "Interlabial Pad", U.S. Appl. No. 10/705,406, Nov. 10, 2003.

(Continued)

*Primary Examiner* — Michele M Kidwell
(74) *Attorney, Agent, or Firm* — Morrison & Foerster LLP

(57) ABSTRACT

The present invention relates to an interlabial pad which is attached between female labia, especially to the pad which can be used together with the sanitary napkin, which has a good sealing efficiency with the labia deepest portion when the user moves and can prevent the chance that the leak of the menstrual blood or the dropping off of the pad is occurred. Further the interlabial pad comprises the absorbing sheet portion facing to the body side upon wearing the pad and the support sheet portion backing the absorbing sheet portion. The absorbing sheet portion includes the absorbent body (13a) which is a stick-shaped or a strip-shaped individual absorbent body and contacts with the neighborhood of the ostium vaginae of the user, the absorbent body (13b) which is a flat-shaped individual absorbent body and contacts with at least of the inner wall of the labia of the user, further said absorbent body for contacting ostium vaginae (13a) is disposed along the substantial center line of the body face side of absorbent body for contacting the inner wall of the labia (13b).

12 Claims, 14 Drawing Sheets

U.S. PATENT DOCUMENTS

| | | | |
|---|---|---|---|
| 5,891,126 A | 4/1999 | Osborn, III et al. | |
| 5,916,205 A | 6/1999 | Olson et al. | |
| 6,355,022 B1 * | 3/2002 | Osborn et al. | 604/385.17 |
| 6,392,117 B1 * | 5/2002 | Mayer et al. | 604/378 |
| 6,890,325 B2 * | 5/2005 | Edens et al. | 604/385.17 |

FOREIGN PATENT DOCUMENTS

| | | |
|---|---|---|
| EP | 0888764 | 1/1999 |
| EP | 1 097 685 A2 | 5/2001 |
| FR | 2703244 | 10/1994 |
| JP | 493722 | 1/1974 |
| JP | 61108258 | 7/1986 |
| JP | 63260556 | 10/1988 |
| JP | 0356366 | 3/1991 |
| JP | 05237151 | 9/1993 |
| JP | 05293138 | 11/1993 |
| JP | 06506368 | 7/1994 |
| JP | 0640203 | 10/1994 |
| JP | 07506035 | 7/1995 |
| JP | 08505797 | 6/1996 |
| JP | 08215242 | 8/1996 |
| JP | 10-33589 A1 | 2/1998 |
| JP | 11514895 | 12/1999 |
| JP | 0051267 | 2/2000 |
| JP | 2000501322 | 2/2000 |
| JP | 2001506170 | 5/2001 |
| JP | 01509402 | 7/2001 |
| JP | 02513633 | 5/2002 |
| JP | 02534163 | 10/2002 |
| TW | 386873 A1 | 4/2000 |
| TW | 524677 A1 | 3/2003 |
| WO | WO-9211825 | 7/1992 |
| WO | WO-93/21879 A | 11/1993 |
| WO | WO-9416658 | 8/1994 |
| WO | WO-9422405 | 10/1994 |
| WO | WO-9500094 A1 | 1/1995 |
| WO | WO-95/17148 A2 | 6/1995 |
| WO | WO-9602217 | 2/1996 |
| WO | WO-97/07763 A | 3/1997 |
| WO | WO-97/17115 A1 | 8/1997 |
| WO | WO-98/08475 A1 | 3/1998 |
| WO | WO-98/57610 A1 | 12/1998 |
| WO | WO-99/01093 A1 | 1/1999 |
| WO | WO-99/01096 A1 | 1/1999 |
| WO | WO-99/26575 A1 | 6/1999 |
| WO | WO-99/55272 A1 | 11/1999 |
| WO | WO-99/56689 A1 | 11/1999 |
| WO | WO-9956681 | 11/1999 |
| WO | WO-0040192 | 7/2000 |
| WO | WO-0147458 A1 | 7/2001 |

OTHER PUBLICATIONS

Mizutani, et al., "Interlabial Pad", U.S. Appl. No. 10/705,408, Nov. 10, 2003.

Mizutani, et al., "Interlabial Pad", U.S. Appl. No. 10/705,780, Nov. 10, 2003.

Mizutani, et al., "Interlabial Pad and Package Thereof", U.S. Appl. No. 10/705,404, Nov. 10, 2003.

Mizutani, et al, "Interlabial Pad and Package", U.S. Appl. No. 10/706,303, Nov. 10, 2003.

Mizutani, et al., "Interlabial Pad", U.S. Appl. No. 10/705,407, Nov. 10, 2003.

Mizutani, et al., "Interlabial Pad", U.S. Appl. No. 10/705,403, Nov. 10, 2003.

Mizutani, et al., "Individual Packaging Body and Outer Vessel Therefor", U.S. Appl. No. 10/705,402, Nov. 10, 2003.

Mizutani, et al., "Interlabial Pad", U.S. Appl. No. 10/705,399, Nov. 10, 2003.

Mizutani, et al., "Interlabial Pad", U.S. Appl. No. 10/705,812, Nov. 10, 2003.

Mizutani, et al., "Interlabial Pad", U.S. Appl. No. 10/705,811, Nov. 10, 2003.

Mizutani, et al., "Interlabial Pad Individual Packaging Body", U.S. Appl. No. 10/705,669, Nov. 10, 2003.

Mizutani, et al., "Interlabial Pad and Package Thereof", U.S. Appl. No. 10/705,400, Nov. 10, 2003.

Mizutani, et al., "Interlabial Pad", U.S. Appl. No. 10/705,778, Nov. 10, 2003.

Mizutani, et al., "Interlabial Pad Individual Packaging Vessel", U.S. Appl. No. 10/705,673, Nov. 10, 2003.

Mizutani, Satoshi, "Interlabial Product Having Form for Finger Securement, and Individual Package", U.S. Appl. No. 10/705,779, Nov. 10, 2003.

Mizutani, et al., "Flap-Equipped Interlabial Pad", U.S. Appl. No. 10/705,670, Nov. 10, 2003.

Mizutani, et al., "Interlabial Pad Individual Packaging Vessel, and Individual Packaging Body", U.S. Appl. No. 10/705,781, Nov. 10, 2003.

Supplementary European Search Report for EP 02771757 Completed Nov. 23, 2004.

Supplementary European Search Report for EP 02 77 1757 Completed on November 23, 2004.

Mizutani, et al., U.S. Office Action mailed Apr. 6, 2007, directed to U.S. Appl. No. 10/705,810; 4 pages.

Mizutani, et al., U.S. Office Action mailed May 28, 2008, directed to U.S. Appl. No. 10/705,810; 10 pages.

\* cited by examiner (a)

(b)

Finger Insertion Direction

INTERLABIAL PAD AND PACKAGE THEREOF

CROSS-REFERENCE TO RELATED APPLICATIONS

This application is a Divisional of U.S. patent application Ser. No. 10/705,810 filed Nov. 10, 2003 which is a Continuation of International Application No. PCT/JP02/04897 filed May 21, 2002, which claims priority to Japanese Patent Application Nos. 2001-152403, filed May 22, 2001, and 2001-291101, filed Sep. 25, 2001. The International Application published in Japanese on Nov. 28, 2002 as WO 02/094161 A1 under PCT Article 21 (2).

BACKGROUND OF THE INVENTION

1. Technical Field

The present invention relates to an interlabial pad, which is used in attachment within female labia, particularly to an interlabial pad, which can be used together with a sanitary napkin, and to a wrapping body that the interlabial pad is contained in a package for wrapping it individually.

2. Background Art

Conventionally, a sanitary napkin and a tampon are used generally as sanitary products for female. However, there have been problems that as for the sanitary napkin used by bringing into contact with garment, it tends to cause the leak of menstrual blood from the gap caused by poor adhesion near the ostium vaginae. While it tends to cause the foreign feeling and the discomfort as for the tampon on the basis of the nature of its products, and it is difficult to fix into the vagina when a user wears it.

Under such situation, sanitary products of the interlabial pad have attracted people as a sanitary product positioned between the sanitary napkin and the tampon in recent years.

The interlabial pad is used by inserting its portion between the labia and bringing into contact with the labia, having advantages that it excels in a wear feeling and is comfortable because of being small as compared with the sanitary napkin, and it is sanitary and clean because the range of the body soiled with menstrual blood is narrow. Moreover, it has characteristics that it is difficult to cause the leak of menstrual blood because of higher adhesion to the body than that of the sanitary napkin, and psychological resistance on wearing the interlabial pad is lower than that of the tampon which is inserted into the vagina.

For example, an interlabial pad 24 as shown in FIG. 2 includes a pair of absorbing panels 26, which comes into contact with at least the inner wall of the labia, and each absorbing panel 26 is bonded its side with each other via a bonding portion 28. In the interlabial pad 24, the absorbing panel 26 comes into contact with at least the inner wall of labia and the bonding portion 28 is inserted into the deepest portion of the labia when a user wears of the pad. The bonding portion 28 closely contacts with ostium vaginae, thereby the menstrual blood flowing out of ostium vaginae can be interrupted and absorbed.

However, in the interlabial pad 24 as shown in FIG. 2, due to the less sealing ability with the deepest portion of the labia when the user is moving wearing the pad, there has been a problem of an occurrence of so-called side leak or a falling of the pad. Since the labia moves in accordance with the movement of the femoral region, the absorbing panel 26 cooperates with the action of the femoral region in walking or in exercising. In accordance therewith, the bonding portion 28 which is bonded with the absorbing panel 26 moves together, and the bonding portion 28 cannot continue to closely contact with the deepest portion of the labia, and a so-called side leak or the falling of the pad occurs.

SUMMARY OF THE INVENTION

In respect of problems described hereinbefore, the object of the present invention provides an interlabial pad having a good sealing efficiency with the deepest portion of the labia when the wearer is in motion and being in capable of preventing from a risk of a so-called side leak and failing of the pad.

To overcome the aforementioned problems, in the present invention, an absorbing sheet portion includes: an absorbent body for contacting an ostium vaginae, which has a stick shape or a strip shape, which is an independent absorbent body, and which contacts neighborhood of the ostium vaginae of a user; and an absorbent body for contacting with an inner wall of the labia, which has a flat shape, which is an independent absorbent body, and which contacts with at least an inner wall of the labia of a user; wherein the absorbent body for contacting with the ostium vaginae is arranged along a substantial center line of the body face side of the absorbent body for contacting with the inner wall of the labia. Therefore, even though the user moves while wearing the pad, it provides the good adhesion of the pad with the deepest portion of the labia and to prevent the pad from a risk of the so-called side leak or from falling of the pad.

Concretely the present invention provides the interlabial pad as follows;

(1) An interlabial pad for attaching thereto in labia, comprising: an absorbing sheet portion facing toward a body side upon wearing the interlabial pad; and a support sheet portion backing the absorbing sheet portion, wherein said absorbing sheet portion includes: an absorbent body for contacting a discharge opening of body fluid, the absorbent body having a stick shape or a strip shape, the absorbent body being an independent absorbent body, and the absorbent body contacting with neighborhood of a discharge opening of body fluid of a user, and an absorbent body for contacting an inner wall of the labia, the absorbent body having a flat shape, the absorbent body being an independent absorbent body, and the absorbent body contacting with at least the inner wall of the labia of the user, wherein the absorbent body for contacting a discharge opening of body fluid is disposed along a substantial center line of the body side surface of the absorbent body for contacting an inner wall of the labia.

The interlabial pad of the present invention comprises an absorbing sheet portion and a support sheet portion backing the absorbing sheet portion. The absorbing sheet portion is arranged to face to the body side while wearing the pad, for example as shown by FIG. 3 and FIG. 4, the sheet portion has an absorbent body 43 for absorbing the menstrual blood and a water-permeable cover sheet 41 for covering surfaces of the absorbent body. On the other hand, the support sheet portion backs the absorbing sheet portion, as shown in FIGS. 3 and 4, has a water-impermeable support sheet 42.

As shown in FIGS. 3 and 4, the interlabial pads of the present invention include an absorbent body 43a and an absorbent body 43b, respectively. The absorbent body 43a is a stick-shaped or a strip-shaped absorbent body which contacts the liquid discharging portion of the user, for example, neighborhood of the ostium vaginae. The absorbent body 43b is a flat shaped independent absorbent body which contacts with at least the inner wall of the labia of the user. Further the absorbent body 43a for contacting ostium vaginae is arranged along a substantial center line 46 of the body face side of the absorbent body 43b for contacting the inner wall of the labia.

The interlabial pads 44 as shown in FIGS. 3 and 4, are folded along the substantial center line 46 upon wearing it, and the pads are attached to the labia. The absorbent body 43a for contacting with ostium vaginae closely contact with the deepest portion including ostium vaginae of the labia, and the absorbent body 43b contacting with the inner wall of the labia comes to closely contact with at least the inner wall of the labia and, in some occasion, further with the pudenda.

In the form, each absorbent body has high degree of freedom and it is difficult to transmit a behavior of one absorbent body to the other absorbent body since the absorbent body 43 is separated into the absorbent body for contacting the ostium vaginae and the absorbent body 43b for contacting the inner wall of the labia. Therefore, the absorbent body 43b for contacting the inner wall of the labia moves in accordance with the action of the femoral region in walking or in exercising, however, the absorbent body 43a for contacting ostium vaginae is not effected by the movement of the absorbent body 43b and can closely contact with the deepest portion of the labia. Therefore, in the case of the user moving, the sealing efficiency between the deepest portion of the labia and the pad comes better to prevent a risk of a so-called side leak or falling of the pad also.

Usually, the menstrual blood discharged from ostium vaginae is absorbed by the absorbent body for contacting with ostium vaginae and closely contacts with the deepest portion of the labia. Particularly in the case that the menstrual blood retention in the uterus or around the uterus cervix (the innermost of ostium vaginae) is discharged all at once by the user's instant moving, a volume of the discharged menstrual blood with a high flow speed flows to the downward of the body (gravitation direction) along the inner wall of the labia. Such rapid and a volume of menstrual blood may overflow the absorbing efficiency of the absorbent body for contacting with ostium vaginae, however, the menstrual blood can be absorbed by the absorbent body for contacting the inner wall of the labia which is arranged at the lower end side of the absorbent body for contacting with the labia, Therefore, the side leak of the menstrual blood can be prevented.

(2) An interlabial pad according to (1), each of the absorbent body for contacting a discharge opening of body fluid and the absorbent body for contacting an inner wall of the labia is covered by respective, independent cover sheet.

For example as shown in FIGS. 3 and 4, the absorbent body for contacting ostium vaginae and absorbent body for contacting the inner wall of the labia may be covered by a single cover sheet 41. As shown in FIG. 5, however, it is preferable that the absorbent bodies 43a and 43b are respectively covered by independent water-permeable sheets 41a, 41b. In comparison with the case of the absorbent bodies being covered by a single cover sheet 41, the degree of the freedom of each absorbent body is increased and it is difficult to transmit a behavior of one absorbent body to the other absorbent body, thereby the sealing efficiency of the labia contacting absorbent body 43a and the deepest portion of the labia while the user moves is improved.

(3) An interlabial pad according to (1) or (2), wherein a bonding area ratio of the absorbent body for contacting a discharge opening of body fluid and the absorbent body for contacting an inner wall of the labia is in a range from 2 to 80% in respect of an area in respect of an apparent area of the absorbent body for contacting a discharge opening of body fluid which is observed from the body side.

Preferably a rate of the bonding area of the absorbent body for contacting ostium vaginae and absorbent body for contacting the inner wall of the labia is from 2 to 80% in respect of an apparent area of absorbent body for contacting ostium vaginae observed from the body side, more preferably in a range from 3 to 30%, particularly preferably in a range from 5 to 10%. If the bonding area is less than the range, the absorbent body for contacting ostium vaginae and absorbent body for contacting the inner wall of the labia are completely separated by the user's action and there is a chance of the pad being incapable of working the function of it. While the area exceeds the range, the freedom degree of each absorbent body is deteriorated, and a behavior of one absorbent body may be easily transmitted to the other absorbent body.

In the specification of the present invention, "the apparent area" means, as shown in FIG. 6, an area S which is multiplied a maximum length L by a maximum width W of the ostium vaginae contact absorbent body 43a which is observed from the body side. The ratio of the bonding area of the absorbent body 43a and the absorbent body 43b (in the case of each absorbent body being covered by the cover sheet 41a, 41b, the bonding area of cover sheets 41a, 41b) in respect of the area S is defined as a bonding area ratio.

(4). An interlabial pad according to any of (1) to (3), wherein a bending stiffness value toward left and right directions of the corporeal body of a bonding portion of the absorbent body for contacting ostium vaginae and the absorbent body for contacting an inner wall of the labia at the center portion of the longitudinal direction of the absorbent body for contacting a discharge opening of body fluid is not more than 1.5 mN.

On the center portion of the longitudinal direction of the absorbent body for contacting ostium vaginae, the absorbent body for contacting ostium vaginae and absorbent body for contacting the inner wall of the labia connect with each other, and preferably a value of the bending stiffness to the right and left direction of the corporeal body of the bonding portion is 1.5 mN or less, more preferably is 1.0 mN or less, and furthermore preferably is 0.5 mN or less in particular. If the value exceeds the above-described range, it is caused possibly that a behavior of one absorbent body is easily transmitted to the other absorbent body since degrees of freedom of each absorbent body deteriorate.

The value of the bending stiffness that is tested by Gurley's Stiffness Tester which is manufactured by Yasuda Seiki Seisakusho is used.

For example, as shown in FIG. 7, the piece including the bonding portion 48 of the labia pad is cut to a size of the vertical direction 25 mm and the horizontal direction 38 mm and set in a fastener 47. Each sinker is set to read a scale at the moment of the piece of the pad leaving from a rotation rod and a bending stiffness of the horizontal direction is evaluated by a conversion formula. In this case, the pad piece is set in the fastener 47 side after the other end portion of the pad piece is so adjusted its length that one end 6.3 mm having a size of the horizontal direction of 38 mm is set in a pendulum 49. Thereby a bending stiffness of a size of 25 mm in the horizontal direction sizes 38 mm and the vertical direction size 25 mm can be tested correctly. In case that absorbent body for contacting ostium vaginae 43a and absorbent body for contacting the inner wall of the labia 43b are bonded with each other at a part of the bonding portion 48, the length of 25 mm of the pad piece including non-bonding portion is cut and may be tested as usually. In case of the piece being not entirely bonded, the bending stiffness of the portion is regarded as zero.

The supplemental sinker is attached to each sinker so that the scale at the moment of the piece leaving from the rotation rod of the pendulum 49 is from 3 to 6. The switch is pressed and the scale is read at the moment of the piece leaving from the rotation rod of the pendulum 49. The test is tried at both ends portions in the horizontal direction described hereinbefore.

The bending stiffness value is obtained by a following conversion formula. Following values (1), (2) and (3) are multiplied, and further are multiplied by 9.88, that is;
(1) an average value obtained from the left side scale and the right side scale,
(2) in case of the position of the hole being 1 inch at the time of setting the sinker, the value is the weight [g] of the sinker, in case of it being 2 inches, twice as weight [g] of the sinker, further in case of it being 4 inches, four times of the weight [g] thereof, each value is respectively added and thereafter obtained value is divided by five, and
(3) the value raised to the second power a substance size 25 mm=1 inch in the horizontal direction is divided by a vertical direction size of 25 mm=1 inch.

Concretely the bending stiffness is calculated by following formula.

Bending stiffness value$[mN]=\{(\text{left}+\text{right})/2\}\times\{(①\times1+②\times2+③\times4)/5\}\times\{L2[\text{inch}]/W[\text{inch}]\}\times9.88\times0.009807$ (While, "left" means a scale obtained from the left side of the piece of the pad, "right" means the scale obtained from the right side of the piece, in case of setting the sinker, ①[g] means the first 1 inch of the position of the whole, ②[g] means 2 inches and (③[g] means 4 inches, further "L" means the substance size 1[inch] of the horizontal direction, and "W" means the size 1[inch] of the vertical direction.)

(5) An interlabial pad according to any of (1) to (4), wherein the absorbent body for contacting a discharge opening of body fluid is in a condition that both ends portions in the longitudinal direction thereof connects with the absorbent body for contacting an inner wall of the labia and that the center portion is not bonded with the absorbent body for contacting an inner wall of the labia.

In the interlabial pad of the present invention, for example, as shown in FIG. 8, preferably the absorbent body for contacting ostium vaginae 43a (or the cover sheet 41a to cover the absorbent body) is in a condition that both ends portions 50 in its longitudinal direction is bonded with the absorbent body for contacting the inner wall of the labia 43b (or the cover sheet 41b to cover the absorbent body), and the central portion 52 is not bonded with absorbent body for contacting the inner wall of the labia 43b (or the cover sheet 41b to cover it). As described hereinbefore, the absorbent body for contacting ostium vaginae 43a is bonded with absorbent body for contacting the inner wall of the labia 43b at the center of the longitudinal direction of the absorbent body for contacting ostium vaginae 43a, and the less bending stiffness value of the bonding portion in lateral direction of the body, the more it is preferable, while the center portion 52 is designed to be in a condition of being non-bonded with absorbent body for contacting the inner wall of the labia 43b, thereby the bending stiffness value can be defined zero. In such embodiment, the freedom degree of each absorbent body is significantly improved that the behavior of one absorbent body can be surely prevented from transmitting to the other absorbent body.

(6) An interlabial pad according to any of (1) to (5), wherein an elastic recovery member is disposed along a front and back direction of the corporeal body of the absorbent body for contacting the discharge portion of the body fluid.

Preferably in the interlabial pad of the present invention, an elastic recovery member is disposed along the front and back direction of the body side of the absorbent body for contacting ostium vaginae. In this embodiment, the absorbent body for contacting ostium vaginae is put in the labia deepest portion which has the highest pinching force and further the elastic recovery member is arranged in the labia deepest portion, thereby the repulsive force of the elastic recovery member affects to the outer pressure or the pinching force between labia. Therefore, the absorbent body for contacting ostium vaginae can closely contact with the labia deepest portion continuously by the reaction in order to prevent the interlabial pad from falling the labia also.

The position where the elastic recovery member is disposed is not limited particularly as far as being disposed along the front and back of the body side of the absorbent body for contacting ostium vaginae. For example, as shown in FIG. 9, the member is preferably embedded in an interior of the absorbent body for contacting ostium vaginae 43a. Thereby the direct transmission of the shape and the repulsive force of the solid elastic recovery member 54 to the inner wall of the labia can be softened by the thickness of the absorbent body for contacting ostium vaginae 43a. Therefore, the inner wall of the labia is prevented from receiving the unnecessary pressure and the user is prevented from a foreign feeling or from damaging the labia. Furthermore, if a polymer composition of the elastic recovery member 54 is dissolved in wearing the labia pad 44, the absorbent body for contacting ostium vaginae 43a absorbs it, and thereby the pad of the present invention is superior in safety for the corporeal body also.

In the specification of the present invention, "elastic recovery member" means, on a base of its elasticity, a material having flexibility together with a shape recovery efficiency that the member is deformed by applying a stress and can recover to the original shape rapidly.

(7) An interlabial pad according to any one of (1) to (6), further comprising a mini sheet piece bonded on the garment side of the support sheet, the mini sheet having one or more bonding portion at each side portion in the longitudinal direction of the support sheet, and having one or more non-bonding portion in the lateral direction of the support sheet, wherein between the mini sheet piece and the support sheet, at least one of said one or more non-bonding portion forms an opening through which the finger is inserted so that the opening of the finger breadth is directly maintained in a surface direction of the support sheet.

In the interlabial pad of the present invention, for example, as illustrated in FIG. 10 or 11, a mini sheet piece 62 may be disposed to form a finger insertion opening 64. In FIGS. 10 and 11, in a lateral direction of the support sheet 42, at least one of both sleeve portions of the mini sheet piece 62 is not bonded with the support sheet 42 surface. Thereby the opening is formed between one sleeve side of the mini sheet piece 62 and the support sheet 42 in a non-bonding condition to form the finger insertion opening 64 which is capable of inserting the finger.

In a longitudinal direction of the support sheet 42, the mini sheet piece 62 is connected with only both lateral sides of the support sheet 42 and is not bonded (adhered) with the inside thereof. Therefore, the mini sheet piece 62 is provided from one lateral side of the support sheet 42 to the other lateral side thereof in a condition of extending over, Therefore, at the portion such extending over from one lateral side to the other, penetrating or non-penetrating space (space for inserting the finger) is formed. Such space can be inserted the finger and keep it.

The word "finger breadth" of this specification does not mean the thickness of the finger but the width direction of the finger in the spread direction of the nail in concrete. "The opening of the finger breadth" means an opening having a sufficient size for inserting the finger.

The opening of the finger breadth is "directly kept" in a direction of the support sheet surface. This means that when the user inserts the finger into the pad normally to wear the pad (the ball of a finger is directed to the garment face side of the support sheet and is inserted to maintain the condition), the pad itself is formed to be adequate for inserting the finger preliminarily. Therefore, the following case excepts from the above described example, such that the opening for the finger breadth is kept in a surface direction by rotating the finger after the person inserts the finger and the opening for the finger breadth is formed on the support sheet surface side secondarily.

As described hereinbefore, in the pad provided with the mini sheet piece, the finger is inserted into the finger insertion opening, thereby the pad can be kept and fixed at the finger for the time being. In this case, the finger insertion opening is formed to be the opening for the finger breadth, and the flat-shaped finger tip is prevented from directing to the different direction in respect of the support sheet and is inserted to contact with the support sheet surface naturally. That is, the finger insertion opening has a wide shape in directions of support sheet surfaces in accordance with the shape of the finger tip of the person to wear. Therefore, the direction where the finger is inserted is determined to detect such that the user is intended to a fix point of the pad by the finger tip. Thereby, as for attaching the pad between labia where the person is difficult to confirm by eyes, the pad can be attached at the adequate position by correctly holding a correct attachment point.

Further in the pad of the present invention, not only the peripheral edge portion of the pad but also the neighborhood to the peripheral edge portion to which the mini sheet piece can be connected are included in "the side portion" in the longitudinal direction of the support sheet.

(8) An interlabial pad according to any one of (1) to (7), wherein the pad is used together with a sanitary napkin.

There have been users to use some of sanitary napkins (as referred to a napkin in following description) laminated with each other for the case of a large volume of menstrual blood. However, there has been a problem of the bad wear feeling such as stiff and it is remarkable to wear the pad from the outer of the garment. To use laminated napkins in the area except ostium vaginae which does not need to be treated by laminated napkins has caused a rash or a sweat. However, when the pad and the napkin are used together, the sanitary product is laminated only around the ostium vaginae, thereby the problem can be solved. Further only the pad can be altered without changing the napkin, thereby the person is prevented from always carrying a remarkable size of napkin.

The sanitary napkin is not only the napkin for absorbing the menstrual blood in a market but also it may include the sheet absorbing the vaginal discharge.

(9) An interlabial pad according to any one of (1) to (8), wherein the interlabial pad is a pad for an incontinence of urine.

According to the interlabial pad of the present invention, the pad can be used as a pad for absorbing incontinence of urine. That is, both ostium vaginae where the menstrual blood is discharged and a urethral meatus where urine is discharged locate between the labia, and the interlabial pad of the present invention to be used between labia can absorb urine also.

As described hereinbefore, the pad of the present invention can absorb urine around labia, especially around the urethral meatus and is useful for the absorbing pad for incontinence, especially for a light incontinence.

(10) An interlabial pad according to any one of (1) to (8), wherein the interlabial pad is a pad for absorbing vaginal discharge.

In accordance with the present invention, the interlabial pad can be used for the pad of absorbing the vaginal discharge. That is, the interlabial pad is used between labia and can absorb the excretion other than the menstrual blood from ostium vaginae for the use Therefore, (for absorbing the vaginal discharge).

As described above, the pad can absorb the vaginal discharge in order to decrease the discomfort for the person, and is useful for the user who is not menstruating.

(11) A wrapping body wherein the interlabial pad according to (1) to (10) is contained in a wrapping container for wrapping it individually.

The interlabial pad is packaged individually and the pad can be carried one by one (every individual packages). As compared with a plurality of pads contained in one package, the pad is kept sanitarily, can be easily carried and can be treated simply.

(12) A wrapping body wherein the interlabial pad according to any one of (7) to (10) is contained in the wrapping container for wrapping the pad individually, the wrapping container has a break seal opening, and the interlabial pad is so contained in the wrapping container that the opening of the pad through which the finger is inserted faces toward the break seal opening of the wrapping container.

As illustrated in FIG. 12, "to provide the finger insertion opening toward the break seal opening of the wrapping body" means that when the wrapping body 72 is opened, the mini sheet piece 62 and further the opening 64 for inserting the finger which is formed by the piece appear, and the finger can be immediately inserted into the opening 64. For example, as illustrated in FIG. 12, the wrapping body 72 can be opened by pulling a tub tape 74, which is provided at the upper surface side of the wrapping container 76, to the right side of the drawing. The finger insertion opening 64 appears at the opening of the wrapping body to open toward the break seal opening. Therefore, the user can insert the finger immediately into the opening 64.

(13) A wrapping body according to (12) wherein the interlabial pad is so contained in the wrapping container that the mini sheet piece is formed in a mountain folded-shaped toward the garment side direction along the substantial center line in the longitudinal direction of the interlabial pad.

"To provide the mini sheet piece in a mountain folded-shape in the garment side direction" means that the sheet is completely folded in forming the garment side to be a convex, and further includes the case that as shown in FIG. 13, the sheet is inflected in forming the garment side to be a convex. As described hereinbefore, the interlabial pad 44 is contained in the wrapping container 76, thereby the folded opening 64 for inserting the finger is naturally opens at the time of breaking the seal. Therefore, the user can confirm easily the part where she inserts her finger so as to achieve more smooth and simple attachment of the pad.

In this embodiment, the mini sheet piece may be a mountain folded shape and it is not required to form whole pad in a mountain folded shape. Therefore, as illustrated in FIG. 13, the wrapping body 72 in which the whole interlabial pad 44 is folded in a mountain folded shape and contained in the wrapping container 76, and as illustrated in FIG. 14, the wrapping body 72, in which only the mini sheet piece 62 is folded in the mountain folded-shaped, while the main body of the interlabial pad 44 is folded in V-shaped toward the garment side and contained in the wrapping container 76, are eligible.

Further the method of breaking the seal of the wrapping container is not limited specifically, as illustrated in FIG. 13 and FIG. 14, the wrapping container 76 of which an upper end side is cut to break it is eligible, further as illustrated in FIG. 15, a wrapping container 76 which is broken the seal from the upper end to both sides (what is called a set of folding doors) is eligible.

BEST MODE OF CARRYING OUT THE PRESENT INVENTION

The preferable embodiment of the interlabial pad in accordance with the present invention will be described with reference to accompanied drawings. In the specification of the present invention, the word "bulkiness" means a size of the direction which the area of the pad projects to contact with an ostium vaginae, "the width" means a size of the lateral direction of the pad and "the length" means a size of the longitudinal direction of the pad.

Figure 1:
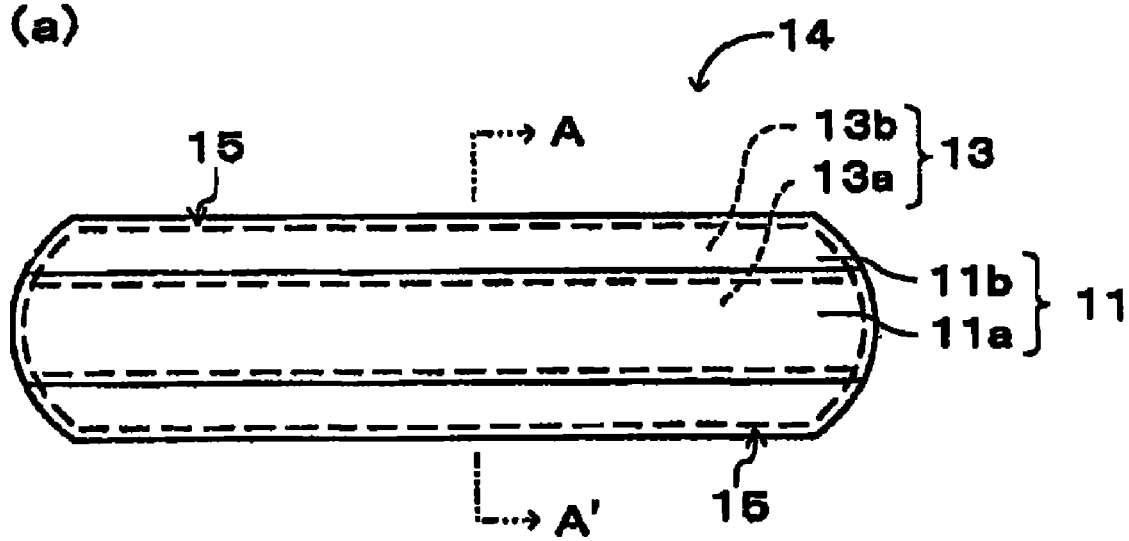
FIGS. 1(a) and 1(b) show a structure of an interlabial pad according to the present invention that FIG. 1(a) shows a top view of the pad and FIG. 1(b) shows a cross sectional view along line A-A' of FIG. 1(a).
Figure 1:
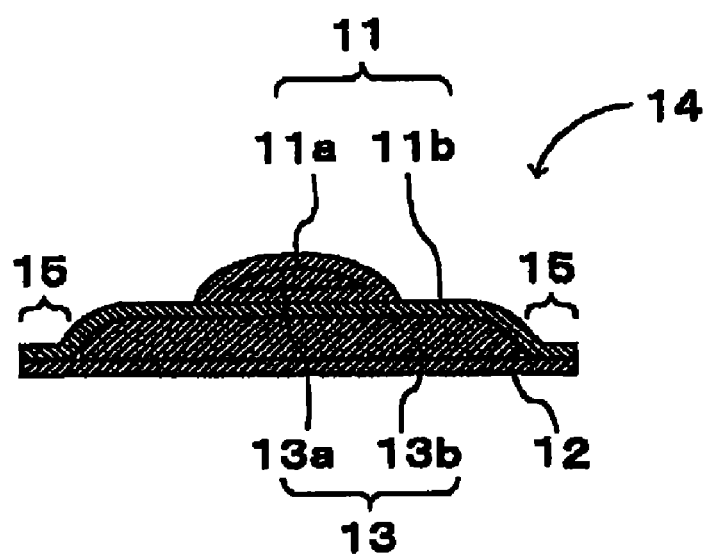
Figure 2:
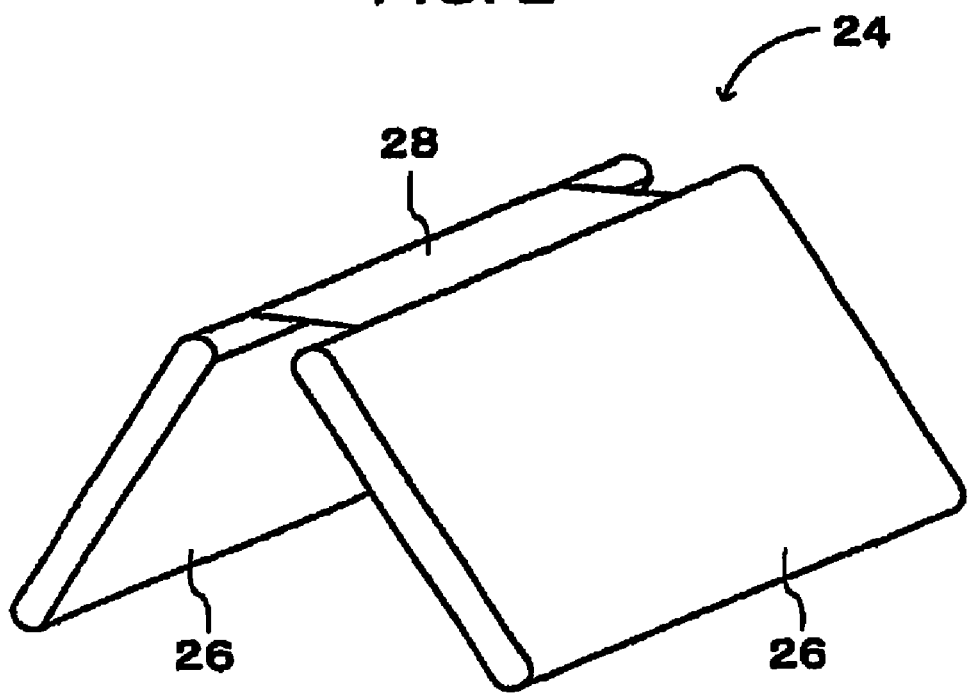
FIG. 2 is a perspective view of a structure of a conventional interlabial pad.
Figure 3:
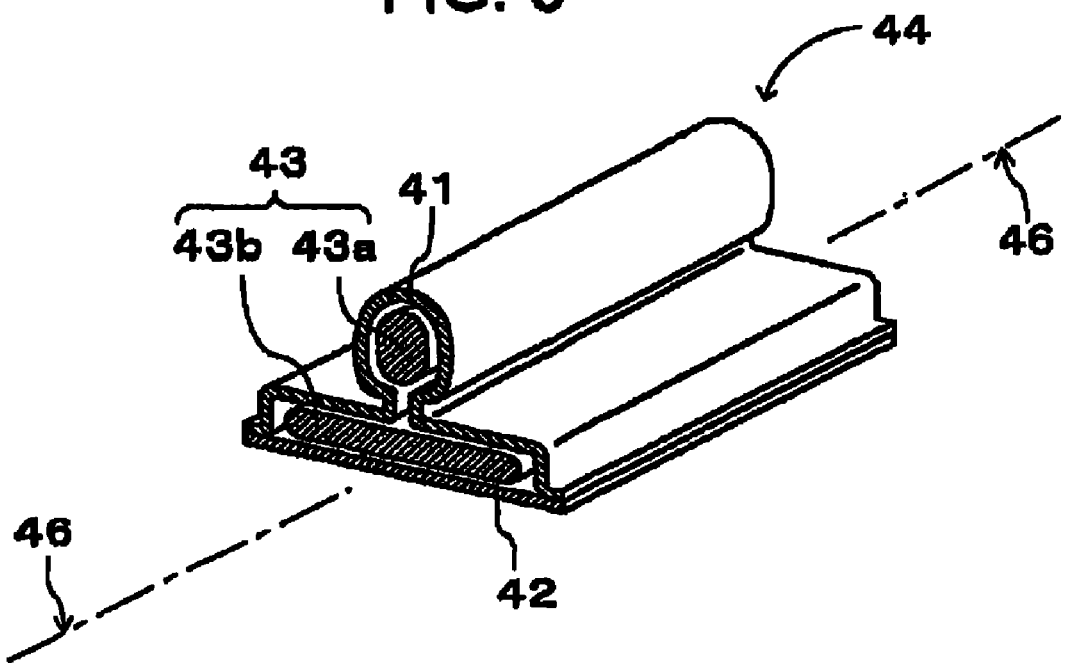
FIG. 3 is a perspective view of a cross section of an interlabial pad according to the present invention.
Figure 4:
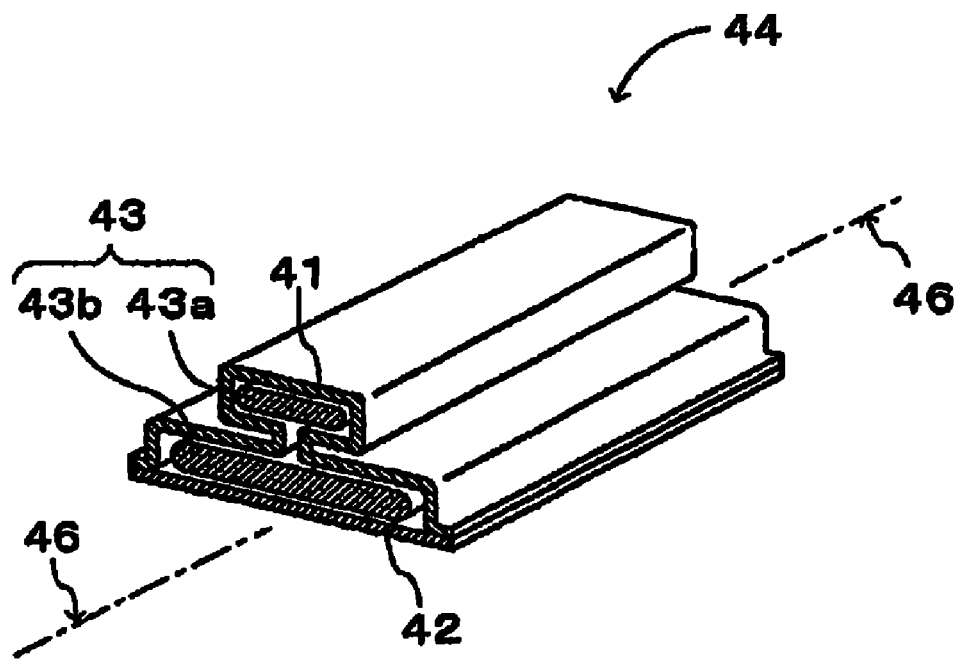
FIG. 4 is a perspective view of a cross section of the interlabial pad according to the present invention.
Figure 5:
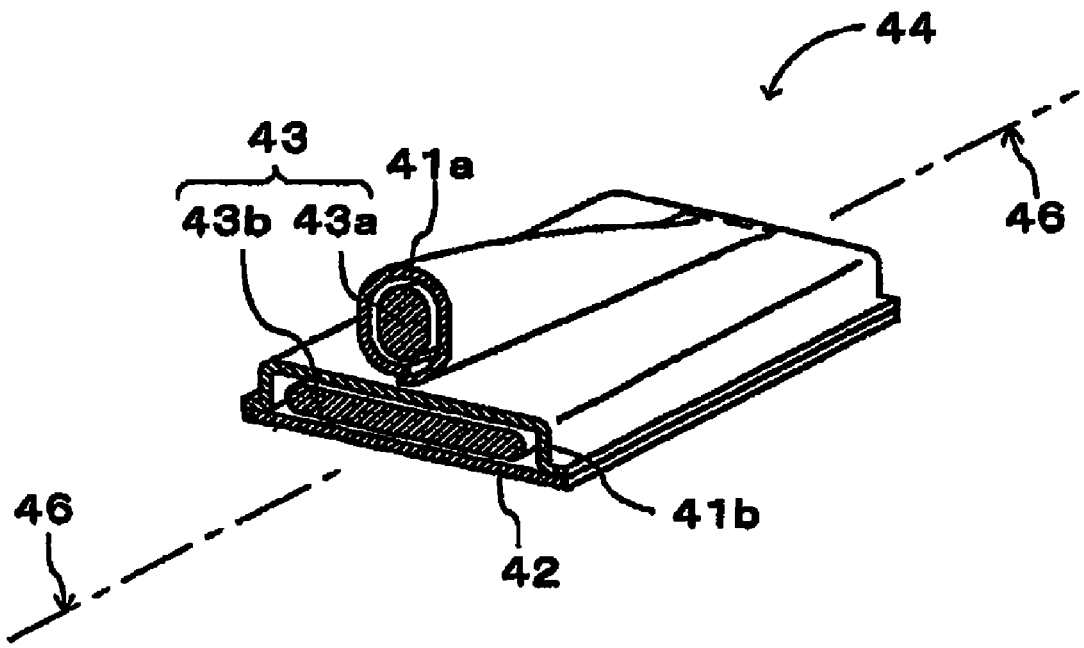
FIG. 5 is a perspective view of the cross section of the interlabial pad according to the present invention.
Figure 6:
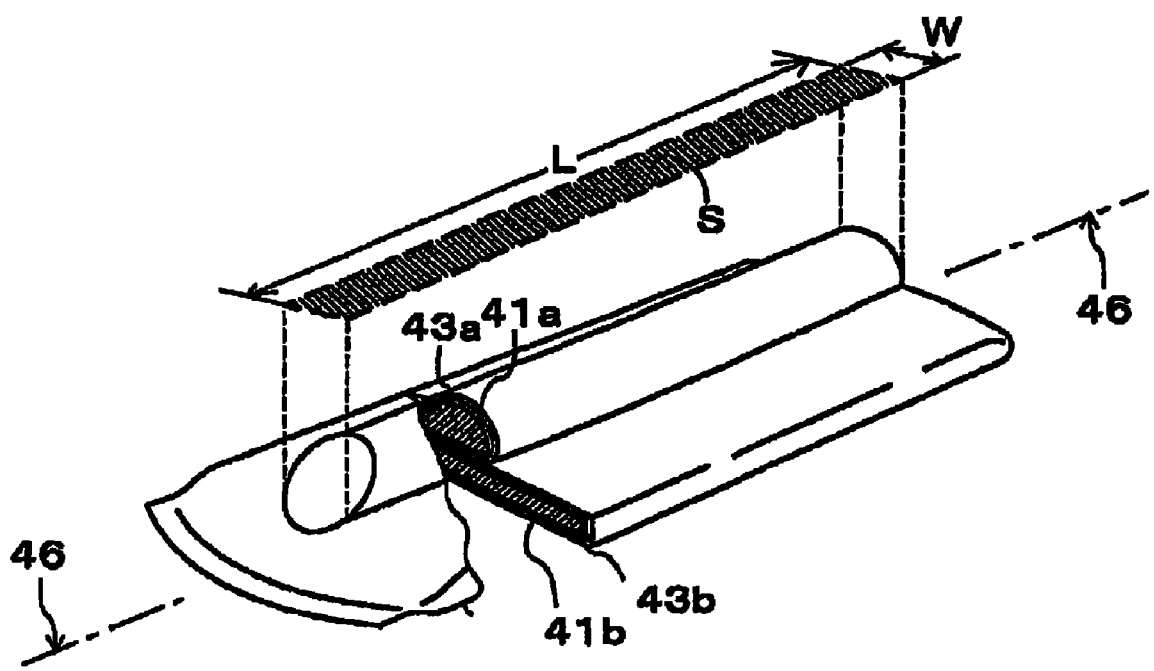
FIG. 6 is a partially cut-away view of the cross section of the interlabial pad according to the present invention.
Figure 7:
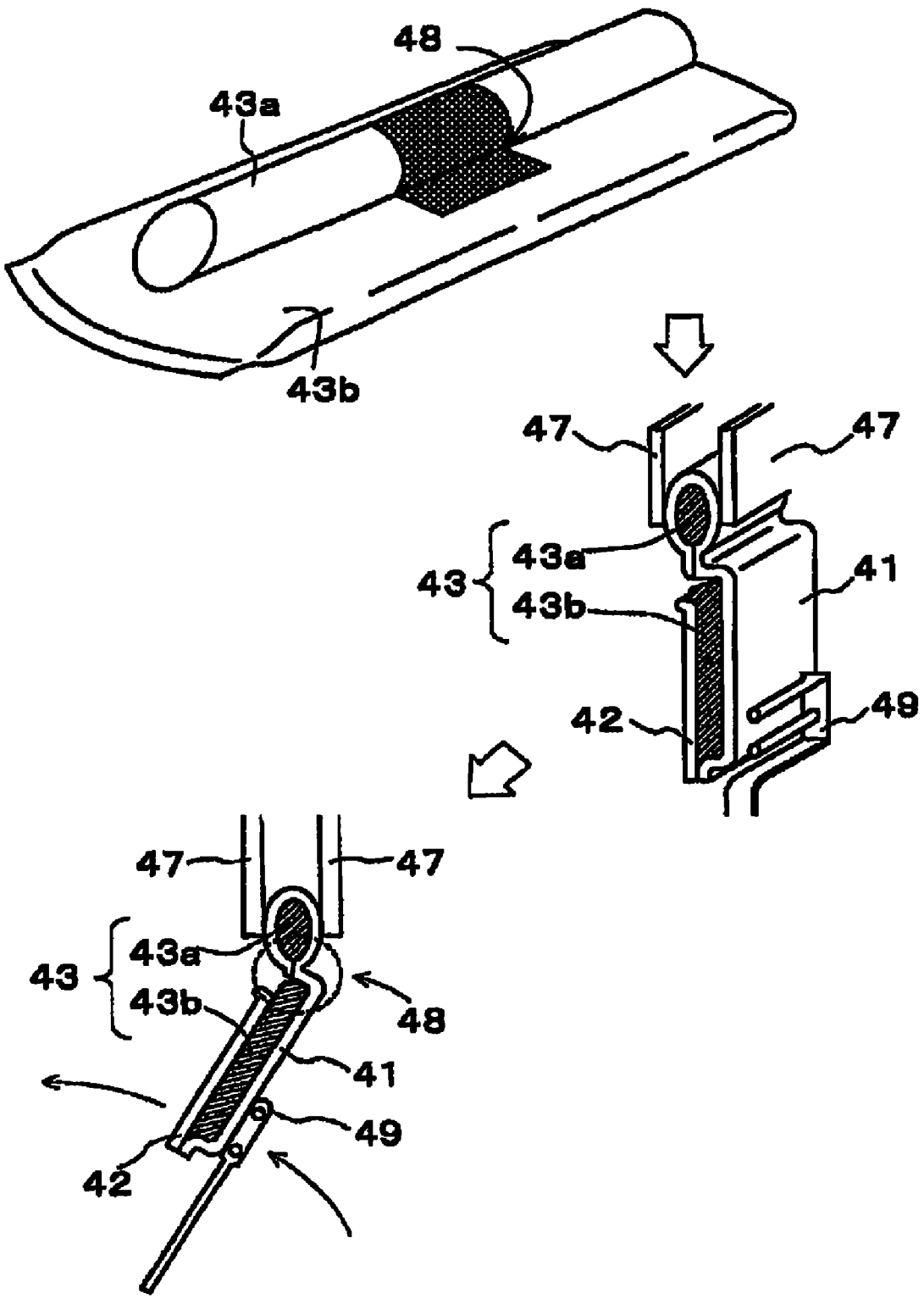
FIG. 7 is a process drawing of a bending stiffness test of the interlabial pad.
Figure 8:
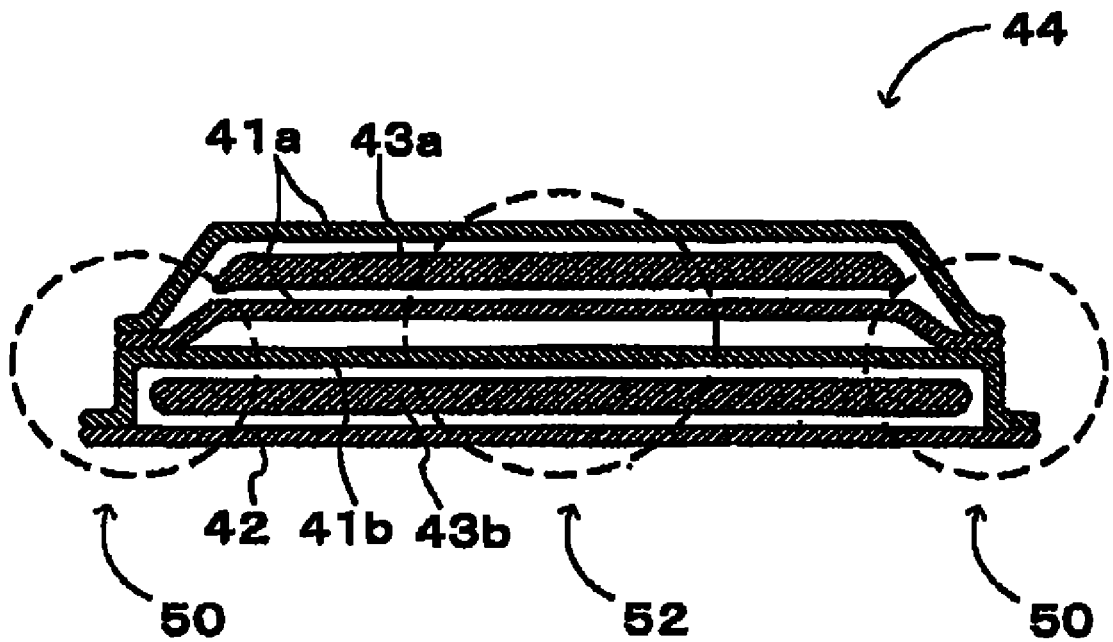
FIG. 8 is a cross section view of the structure of the interlabial pad according to the present invention.
Figure 9:
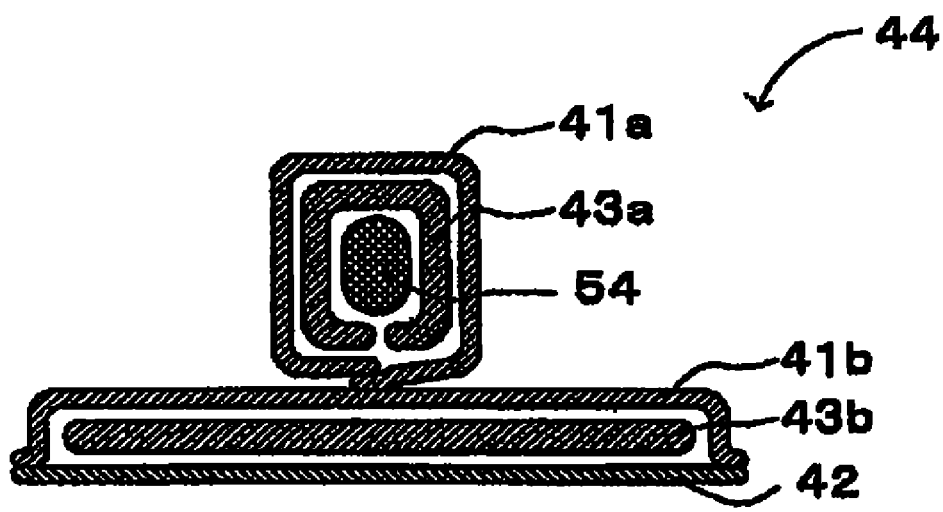
FIG. 9 is a cross section view of the structure of the interlabial pad according to the present invention.
Figure 10:
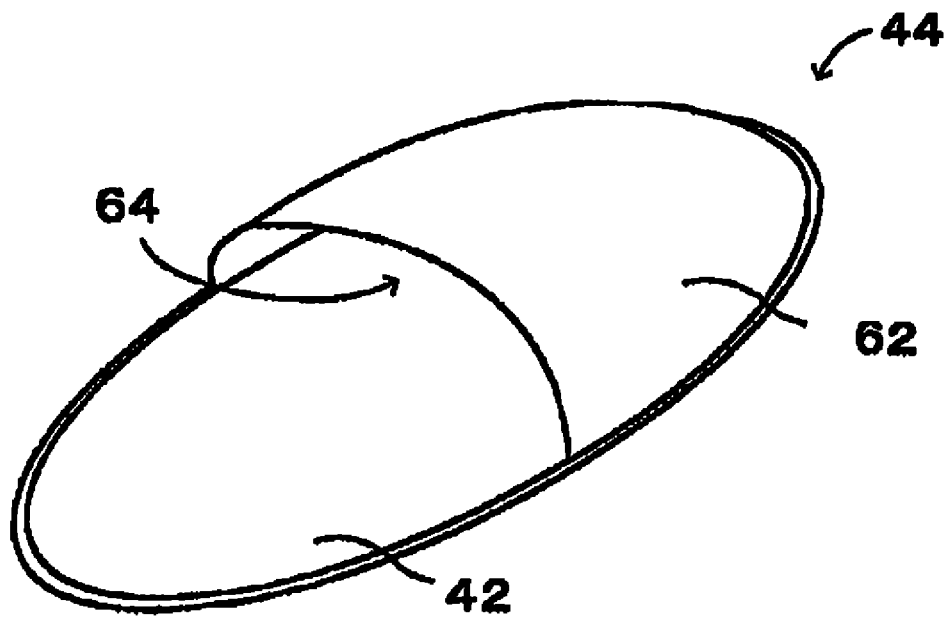
FIG. 10 is a perspective view of the structure of the interlabial pad according to the present invention.
Figure 11:
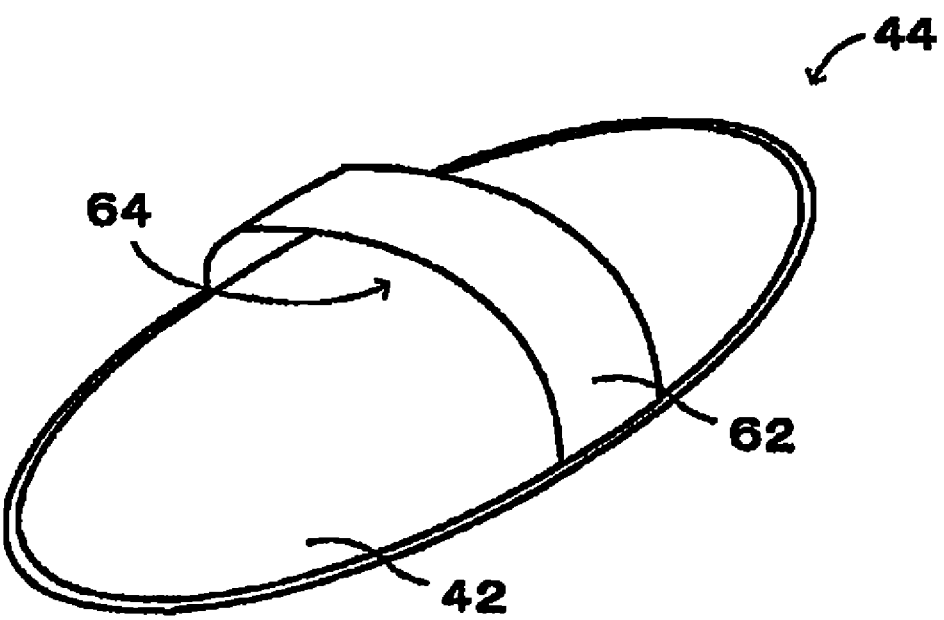
FIG. 11 is a perspective view of the structure of the interlabial pad according to the present invention.
Figure 12:
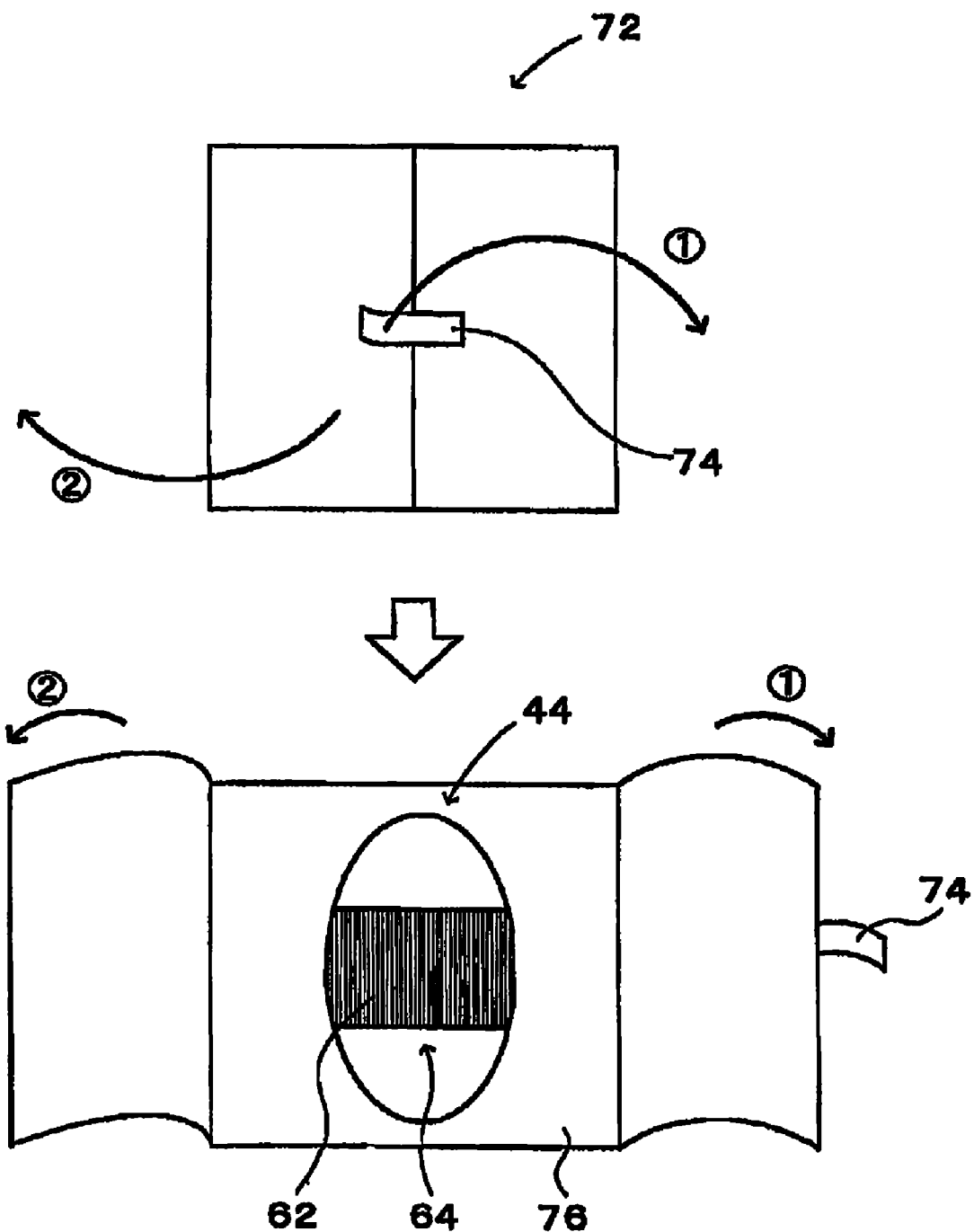
FIG. 12 is a process drawing of a method of sealing off a wrapping body according to the present invention.
Figure 13:
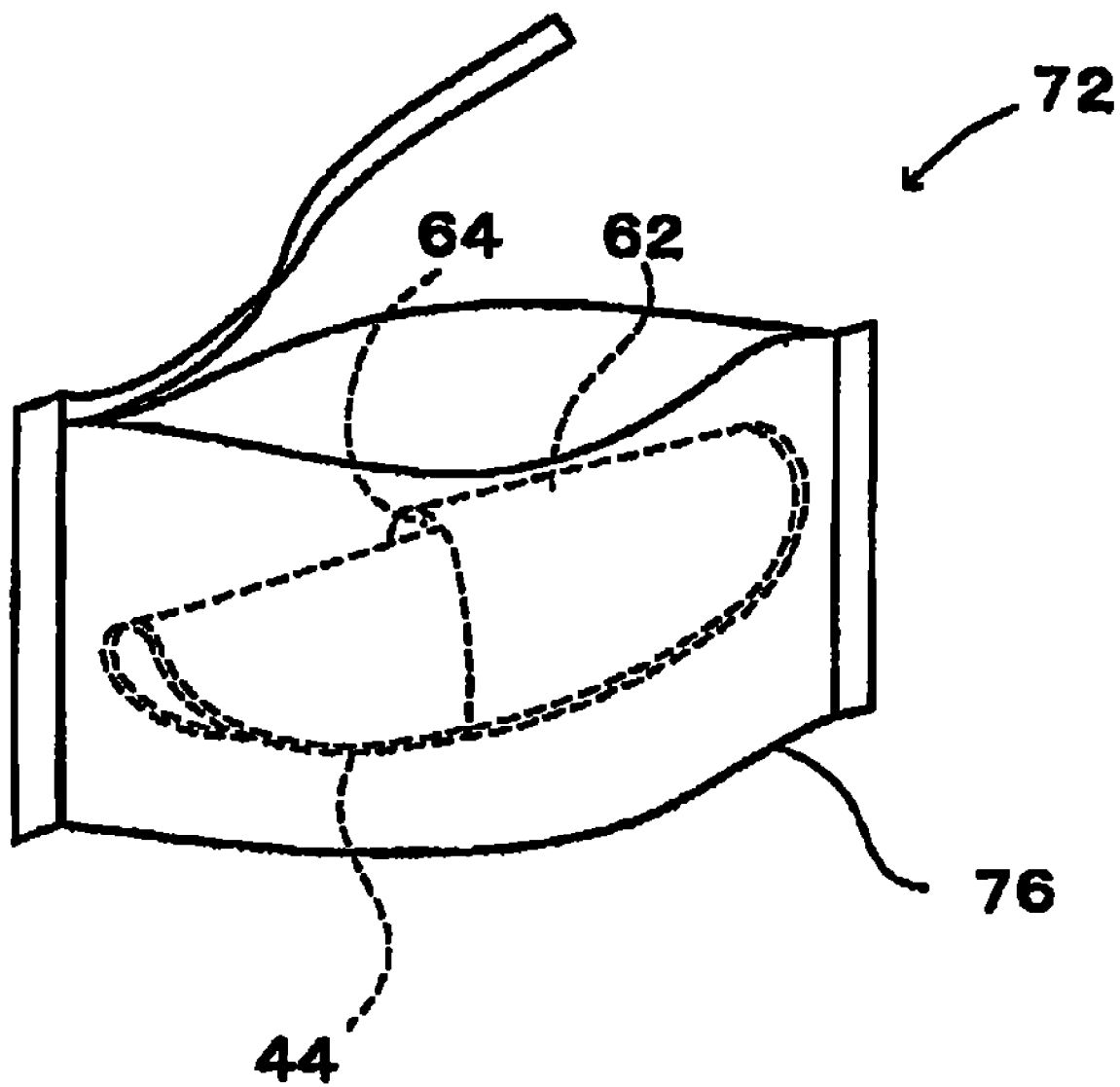
FIG. 13 is a perspective view of the structure of a wrapping body according to the present invention.
Figure 14:
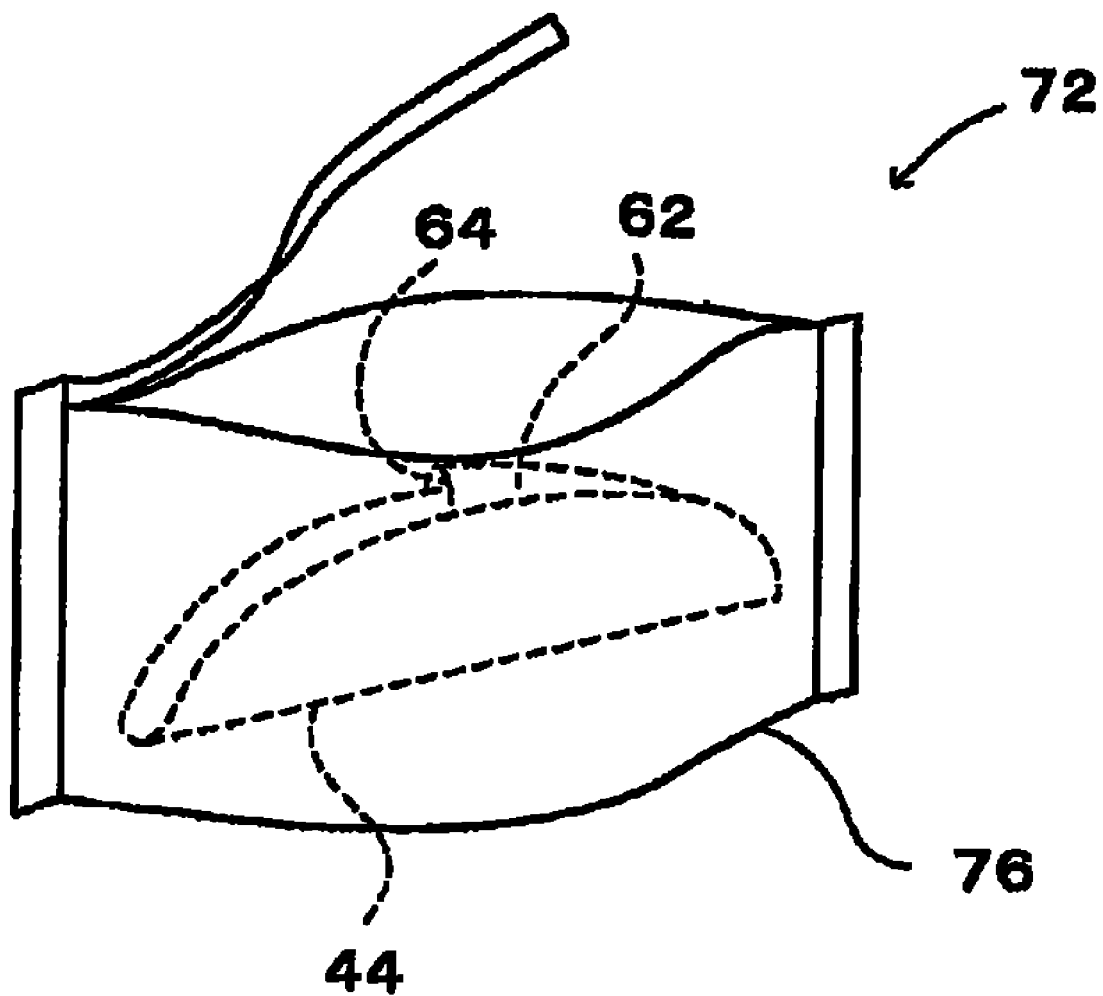
FIG. 14 is a perspective view of a structure of the wrapping body according to the present invention.
Figure 15:
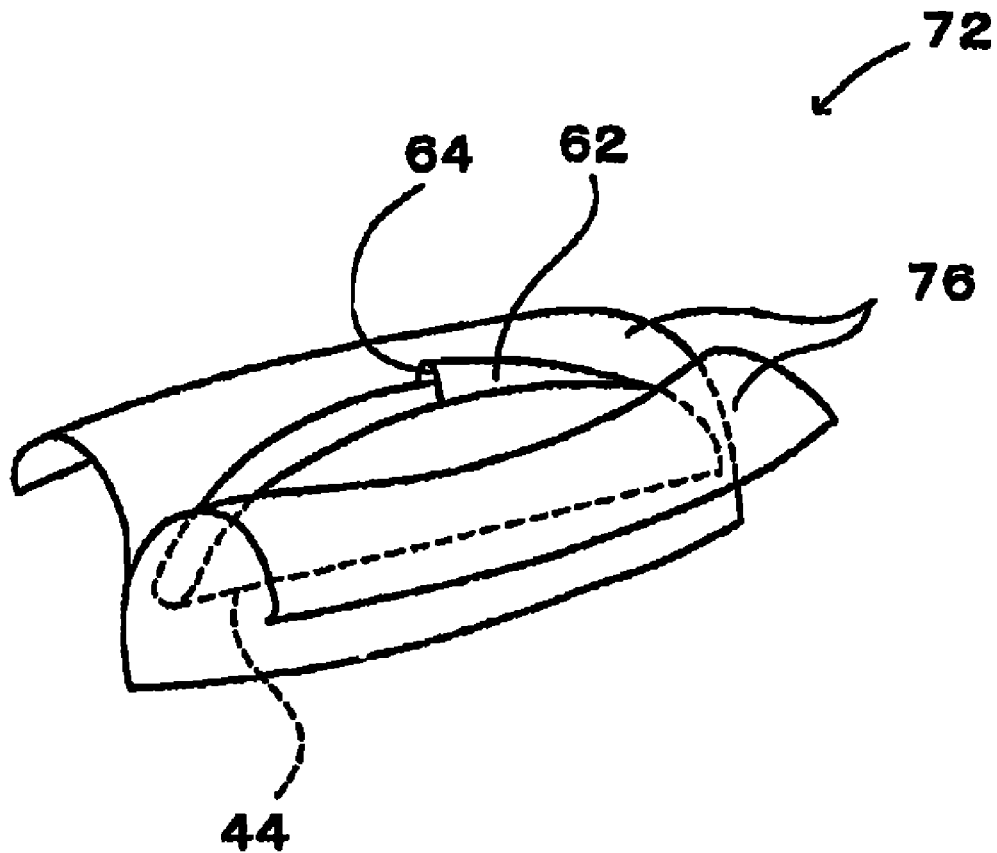
FIG. 15 is a perspective view of a structure of the wrapping body according to the present invention.

FIG. 1 is a cross section view of a structure of an interlabial pad 14 according to the present invention that (a) shows a top view of the pad and (b) shows a cross sectional view along line A-A' of (a).

[(A) Structure of a Basic Interlabial Pad]

As shown in FIGS. 1(a) and 1(b), a basic interlabial pad 14 of the present invention includes an absorbing sheet portion and a support sheet portion backing the absorbing sheet portion. The absorbing sheet portion includes an absorbent body 13 for absorbing at least menstrual blood, the surface of which is covered by a water-permeable cover sheet 11 if desired, and is used to face against the body side upon wearing the pad. The absorbing sheet portion is a stick-shaped or a strip-shaped independent absorbent body and includes an absorbent body for contacting ostium vaginae 13a and an absorbent body for contacting an inner wall of the labia 13b, wherein the absorbent body 13a contacts around ostium vaginae of the user and the absorbent body 13b contacts with at least the inner wall of the labia of the user. The absorbent body for contacting ostium vaginae 13a is disposed along the substantial center line of the body face side of the inner wall of the labia absorbent body 13b. While the support sheet portion 14b comprises a water-impermeable support sheet 12.

The whole configuration of the interlabial pad 14 is eligible as long as it attaches to the labia, and is not limited to the specific one. However, it is preferable to form it into a substantial oblong shape, for example, to an elliptic types an ovoid type, a gourd-shape, a drop-shape and the like. Preferably the length of the pad 14 is 50 to 150 mm, more preferably 80 to 120 mm. If the length is greater than the range, the area exceeding from the labia scrapes with the napkin and the underwear, and resultantly the friction which is caused by scrapping to cause a chance of falling of the pad from the labia. If the length is less than the range, the bonding area with labia surface is also decreased to cause a chance of falling of the interlabial pad from labia in accordance with the movement of the user.

Preferably a width in appearance (the length in the lateral direction) of the inner wall of the labia absorbent body in respect of the absorbent body for contacting ostium vaginae from the body side of the absorbent body for contacting ostium vaginae is in a range from 150 to 600%. Furthermore the width in appearance of absorbent body for contacting the inner wall of the labia is from 10 to 60 mm, preferably in a rage from 20 to 40 mm, thereby the absorbent body for contacting ostium vaginae closely contacts with the deepest portion of the labia and absorbent body for contacting the inner wall of the labia closely contacts with the inner wall of the labia to cover the outer labia. Such shape of the pad can absorb the menstrual blood more certainly since the pad is worn so that absorbent body for contacting the inner wall of the labia comes to cover the outer labia and the absorbing surface of absorbent body for contacting the inner wall of the labia is positioned vertically in respect of a rapid and a volume of menstrual blood which flows to the downward direction of the body (gravity direction).

The width in appearance of the absorbent body for contacting ostium vaginae from the body side is preferably in a range from 1.5 to 40 mm, more preferably from 3 to 25 mm. If the width is less than the range, there is a chance of the absorbing efficiency of the absorbent body for contacting ostium vaginae to be deteriorated, while if it is greater than the range, since the contacting area of the absorbent body for contacting ostium vaginae with the inner wall of the labia will be increased and the behavior change of the inner wall of the labia is transmitted to the ostium vaginae contacting absorb layer, the sealing efficiency of the absorbent body for contacting ostium vaginae in respect of the labia deepest portion may be damaged. The cross sectional shape of the absorbent body for contacting ostium vaginae is round-shaped, oval-shaped, triangle-shaped, rectangular-shaped, donuts-shaped (hollow-shaped) and the like, and not limited particularly, however, it is preferable to be oval-shaped, or hollow oval-shaped so that the absorbent body closely contacts continuously sealed with the labia deepest portion during the steps of wearing or in a time of wearing to progress the pad into the labia.

The size of the absorbent body 13 contained in the cover sheet 11 is preferably comprised to be smaller from 2 to 10 mm than the outline of the cover sheet 11 in order to prevent the peripheral portion from being hard to deteriorate the wear feeling at the time of which is contained in the cover sheet 11.

For a method of bonding the absorbent body for contacting ostium vaginae 13a with absorbent body for contacting the inner wall of the labia 13b (or the cover sheets 11a, 11b to cover them), the individual or a combination of adhering by a heat embossing or an adhesive can be used. In consideration of using the interlabial pad 14 (wet condition by the menstrual blood), it is preferable to connect aforementioned each absorbent body (or the cover sheet to cover them) by a heat embossing or by a combination of the heat embossing and the adhesive. For the adhesive used for the pad, a pressure sensitive adhesive made up mainly of a synthetic rubber such as non water soluble styrene-ethylene-butadiene-styrene block copolymer (SEBS), styrene-butadiene-styrene block copolymer (SBS), styrene-isoprene-styrene block copolymer (SIS) and the like, the heat sensitive adhesive made up mainly of a thermoplastic resin such as ethylene-vinyl acetate copolymer (EVA) and the like, the adhesive made up mainly of water soluble thermoplastic resin (such as poly vinyl alcohol (PVA)), water sensitive gel made up mainly of a starch glue, or acrylic acid and comprised of the chemical stimulation the plasticizer or a water included therein, non water sensitive gel made up mainly of a silicone and comprised of the chemical stimulation and the plasticizer included therein, are eligible. For disposing the adhesive, a surface type, a dot type, a mesh type, a stripe type and the like may be selected accordingly.

[Cover Sheet]

Preferably the cover sheet is selected from water-permeable and non-stimulate materials. For example a non-woven fabric obtained by a manufacturing method such as a melt blown, a spun bond, a through air, a point bond, a needle punch, a spun bond and the like, can be used, while in consideration of a contacting ratio with the inner wall of the labia, it is preferable to use an individual or a combination of non-woven fabric obtained by manufacturing method such as a spun lace, a melt blown, a needle punch and the like.

It is also preferable to use an individual or a mixed sheet-shaped fiber which is selected from a rayon, an acetate, a cotton or a pulp such as a natural fiber, or a single fiber or combined fiber having a sheath-core structure comprising a synthetic resin, a hydrophilic treated synthetic fiber and the like. Concretely a spun lace non-woven fabric and the like is eligible so that fibers mixed with a synthetic fiber in an amount from 10 to 1% by mass, a natural cotton in an amount from 4 to 30% by mass, a rayon or an acetate in an amount from 60 to 95% by mass, are adjusted in a range from 20 to 50 g/m² based on the specific per unit area of composition, thereafter fibers are confounded by a water flow confounding and are dried to adjust the thickness from 0.1 to 1.0 mm.

In order to keep the bulkiness and the distance between fibers in the case of the cover sheet contacting with the menstrual blood, the synthetic fiber is compounded in the spun lace non-woven fabric. Further the compound ratio of the synthetic fibers is slightly low, because even though the menstrual blood wets the sheet, its single fiber strength is maintained and there is a chance of damaging the inner wall of the labia by high single fiber strength if the synthetic fiber is compounded more than necessary. It is preferable that the synthetic fiber is a single fiber such as PP, PE, PET and the like, or a fiber formed by a graft polymer of PE and PP, a compound synthetic fiber having a sheath-core structure which the core portion is PP or PET, and the sheath portion is PE, a decentering-shaped sheath-core structure, a side-by-side structure. Further it is also preferable to use a milky fiber by mixing filler in an amount from 0.5 to 10% by mass which comprises a titanium oxide and a calcium carbonate if desired.

The fiber which is used for aforementioned spun lace non-woven fabric is a natural cotton having a fiber length in a range from 15 to 60 mm, a rayon or an acetate having a fiber length in a range from 25 to 51 mm and is selected from its fineness in a range from 1.1 to 6.6 dtex. In this embodiment, the bonding area with the inner wall of the labia can be increased by using fibers having much of surface area, and it is preferable to decrease the chance of falling of the pad from the labia. For example it is preferable to use rayon or acetate having a different-shaped cross sectional form such as a Y-shaped or C-shaped fiber cross-section. In comparison with a circular-shaped fiber, in the different-shaped cross sectional fiber, the surface area is increased and a clearance between fibers is increased to deteriorate the strength value of the cover sheet, thereby the sealing efficiency of the pad with the inner wall of the labia is improved and it is also preferable to decrease a chance of falling of the pad from the labia or of a leak of the menstrual blood.

For another example of preferable cover sheet, it is eligible to use the spun lace non-woven fabric in an amount from 20 to 50 g/m² based on the specific weight per area of composition which is compounded by a ratio of a synthetic fiber in an amount from 15 to 5% by mass, a natural cotton in an amount from 50 to 10% by mass, further rayon or an acetate in an amount from 35 to 85% by mass, which is widened from 10 to 80% in a width direction and is enlarged from 10 to 80% in a longitudinal direction. This spun lace non-woven fabric has high rough and fine slope in a plane condition and the confound between fibers get loose once, thereby each fiber, particularly a synthetic fiber having a high strength of single fiber is spring backed to have substantial loop-shaped fibers which protrude to the inner wall of the labia side.

This protruding substantial loop-shaped fiber can soften the frictional resistance in a shear direction on the inner wall of the labia and the pad surface, thereby it is not only to decrease a chance of damaging the inter inner wall of the labia but also to decrease a flow speed of the menstrual blood which flows along the substantial flat-shaped inner wall of the labia toward the underwear, and the menstrual blood can be transferred to the absorbent body in an interior of the pad.

The height and a pitch of the substantial loop-shaped protrusion can be controlled by changing a widening ratio and a stretch ratio of non-woven fabric, by changing a confounding force between fibers in accordance with a manufacturing method of non-woven fabric, or by using a compound synthetic fiber having a decentering core-shaped sheath-core structure or a side-by-side structure as a synthetic resin, in which crimp ratio of each single fiber is adjusted in use of a difference of a heat shrink ratio between resins.

For another example of preferable cover sheet, a thermoplastic film is perforated by a perforation or a heat press, or a sheet compounded of the film and the non-woven fabric are eligible. Particularly, the sheet provided with a lot of raising fine protrusions by a water jet treatment on the non-woven fabric portion of the compound sheet is preferable. The surface resistance caused by the protrusion can decrease a flow speed of the menstrual blood on the cover sheet surface to stop and absorb the flow of the menstrual blood certainly. Preferably the height and the distance of protrusions are in a range from 0.1 to 4 mm. If the height is less than the range, the menstrual blood cannot be certainly absorbed since the clearance of the pad interior into which the menstrual blood enters comes to be narrow, while if it is greater than the range, there is a chance of putting the protrusion down by a body pressure in wearing the pad, and these are not preferable.

The cover sheet may be perforated partially or entirely and the perforation ratio is preferable in a range from 3 to 30%. If the ratio is less than the range, an effect of transferring the menstrual blood to the absorbent body side is deteriorated, while if the ratio is greater than the range, there is a chance of falling of the pad from the labia due to a deteriorated contact ratio with the inner wall of the labia, and these are not preferable.

Among the materials, considering the liquid mobility from the inner face of the labia, chemical stimulation by an activator, and adhesion with the inner wall of the labia, it is preferable to laminate rayon with 1.1 to 4.4 dtex fineness and 7 to 51 mm fiber length by 40 to 80% of a total specific weight per unit area on the body face side, and to laminate a mixture of rayon with 1.1 to 4.4 dtex fineness and 7 to 51 mm fiber length by 14 to 42% of a total specific weight per unit area and PET with 1.1 to 4.4 dtex fineness and 7 to 51 mm fiber length by 6 to 18% of a total specific weight per unit area on the garment face side. After laminating them so that the total specific weight per unit area of the two layers becomes 20 to 60 g/m$^2$, the fibers are entangled by water-flow interlacing treatment and then dried to prepare spun lace non woven fabric with the thickness of 0.13 to 0.50 mm. The spun lace non woven prepared as described is preferable. At this time, by mixing PET on the garment face side, bulkiness can be easily maintained even if the water permeable sheet becomes wet. Therefore, adhesion to the inner wall of the labia can be maintained.

[Absorbent Body]

The absorbent body may be capable of keeping and absorbing a liquid (the menstrual blood) and preferably may be bulkiness, may hard to deform and may be less chemical stimulation. For example, it adequately compounds of a particle-shaped pulp, a rayon, an acetate, a natural cotton, a chemical bond treated air laid pulp, a super absorbent polymer, a fiber-shaped super absorbent polymer, a synthetic fiber and the like. Further the sheet-shaped absorbent body is eligible which is the same as described in the cover sheet.

It is preferable for the absorbent body, although any material can be used as long as it is capable of absorbing and holding liquid (body fluid), to be bulky, hard-to-be deformed, less chemically stimulant, and highly flexible to fit into the labia. Specifically, a non woven sheet in which, 50 to 150 g/m$^2$ of pulp selected from the range of the fiber length of 1 to 10 mm is laminated on the garment face side and, on the body face side, 150 to 250 g/m$^2$ of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted embossing to have 2 to 10 mm bulkiness, and more preferably to have 3 to 5 mm bulkiness. Thereby, liquid can be easily transferred from the body face side to the garment face side resulting in the improvement of the absorbing and holding capacity. Furthermore, by providing a mesh spun lace non woven fabric of rayon with 1.1 to 4.4 dtex fineness and 25 to 51 mm fiber length by a specific weight per unit area of 15 to 40 g/m$^2$, the liquid transferred from the body face side can be diffused by the mesh spun lace to be induced to almost all over the region of the pulp layer. Therefore, more liquid can be effectively absorbed.

[Support Sheet]

In case of using the water permeability material, the same material, which is used for the cover sheet, is eligible. In this case, it prefers to use the pad together with a sanitary napkin (a pad used together with the sanitary napkin);

Further if non-water permeability material is used, the menstrual blood, which is kept in the absorbent body, is prevented from a leak out of the interlabial pad. Furthermore the pad can be comprised of water vapor permeability material, thereby in wearing the pad, the sweat and the discomfort can be decreased.

To apply materials of non-water permeability, non-water permeability film such as a thin filmed synthetic resin of PE, PP and the like, a porous film comprised that a synthetic resin is filled with inorganic filler and provided with an extension treatment, a laminate film compound of a paper or non woven fabric and non-water permeability film, water repellent, a porous resin film is connected on a rear surface of the non woven fabric of a spun bond or a spun lace which are treated with a water repellent, are eligible. Further for a method of providing ventilation on non-water permeability sheet, it is eligible to form a capillary having 10 to 30% rate of the hole area and a pore size of 0.1 to 0.6 mm toward the absorbent body.

More concrete example of applying non-water permeability materials, a film mainly of a low density polyethylene (LDPE) is eligible which is obtained from a range of a density 0.900 to 0.925 g/cm$^3$, in an amount from 15 to 30 g/m$^2$ by mass, based on the total mass per unit area of the composition. The flexibility not to hurt a wear feeling is considered. More preferably, during the pad is attached between labia, to decrease a chance of dropping the interlabial pad from the labia due to the high friction, when non-water permeability sheets are contacted with each other, with the pad which is used together or with the under wear, the film is treated an embossing process and the convex upheaval portion is disposed, thereby it may decrease a ratio contact by less friction drag.

[Elastic Recovery Member]

For the elastic recovery member, a foaming member such as an elastomer component, polyethylene foam can be used in a single or compounded in a predetermined ratio. Concretely it is preferable to include an elastomer compound in an amount from 10 to 90% by mass, preferably from 15 to 60% by mass. It is less than 10% by mass, a sufficient compression recovery ratio cannot be obtained, while it is greater than 90% by mass, the compression recovery ratio cannot be significantly improved, and furthermore there is an inconvenience to be difficult to form a sheet.

For example, polyester type, urethane type, olefin type, styrene type, polyamide type thermoplastic elastomer, a low density polyethylene using a metallocenes catalyst, ethylene-α-olefin copolymer are eligible for an elastomer compound and may be used in a single or be compounded adequately.

A compound of aromatic polyester for a hard segment and an amorphous polyester or aliphatic polyester for a soft segment is eligible for a polyester type elastomer. A polyurethane elastomer is obtained from a polyester, low molecular glycol, methylene-bisphenyl-isocyanete and the like and concretely a polylactone esterpolyol which is added and polymerized polyisocyanete in the presence of a short chain polyol.

An ethylene-α-olefin random copolymer and diene copolymer as the third compound polymerised with the copolymer are eligible for an olefin type elastomer. A block copolymer such as SEBS, SIS, SEPS, SBS are eligible for a styrene type elastomer. For a polyamide type elastomer, a compound of a nylon for a hard segment and a polyester or a polyol for as soft segment is eligible.

For a stable molding of elastic member, a high-density polyethylene, a low-density polyethylene, or line-shaped low density polyethylene may be compounded in a polymer for an elastomer compound. Further an antiblocking agent, an ultraviolet absorbent body, a viscosity branch improver, a flatting agent and other kinds of improver can be compounded.

The elastic recovery member may be fiber-shaped compound. The fiber-shaped compound can be made from an elastomer composition or anti-elastomer composition and it is preferable that the obtained elastic member is superior in compression recovery efficiency and fibers can be melted by a heat in molding. For anti-elastomer composition in fiber-shaped compound, for example, a polyester type composition such as polyethylene terephthalate, polybutylene terephthalate and the like, olefin type composition such as polyethylene, polypropylene and the like, further nylon, acryl and the like are eligible. Further an ultraviolet absorbent body, a viscosity branch improver, a flatting agent, a coloring agent and other kinds of improver may be compounded in a composition polymer of an anti-elastomer composition.

The cross sectional shape of the elastic recovery member is a round-shaped, an oval-shaped, a triangle-shaped, a rectangular-shaped, a donuts-shaped and the like, and not limited particularly, however, the width in unloading is preferable to be in a range from 1 to 10 mm. If the width is less than the range, the repulsive force of the elastic recovery member in respect of a pinching force of the labia in wearing the pad is completely softened by the absorbent body and the chance of dropping off the pad will be increased. While it is greater than the range, the elastic recovery member is folded in inverse letter V type in wearing the pad and the buckling repulsive force occurs on the member. The buckling repulsive force is a force toward one direction and the force concentrates to the direction, thereby the user comes to have a foreign feeling, further there is a chance of damaging the labia.

Preferably the amount of the member is in a range from 10 to 100 g/m² based on the total mass of composition. If the amount of the member is less than the range, the compression recovery ratio or the repulsive force of the elastic recovery member will be deteriorated and a chance of dropping off the pad will be increased. While the amount will be greater than the range, the strength of the pad will be increased to provide the user a foreign feeling.

Preferably the compression recovery ratio of the elastic recovery member is greater than 50% and the repulsive force is in a range from 490 to 4900 Pa in a time of the compression. If these are less than the range, the repulsive force is completely softened by the absorbent body. While these are greater than the range, the inner wall of the labia is pressed unnecessarily to provide the user a foreign feeling and there is also a chance of damaging the labia.

By using KES compression characteristics FB-3 AUTO-A Tester (commercial name) of Kato Tech, the compression recovery ratio and the repulsive force are measured under the condition of setting the test piece cut into 100 mm×100 mm on the testing basement in the terminal area of 2 cm², a maximum load 4900 Pa, and a velocity of 50 sec/mm.

[Mini Sheet Piece]

The mini sheet piece is a sheet-shaped composition such as a woven fabric and non-woven fabric, a plastic sheet and is not limited particularly, however, it is preferable to be a sheet-shaped composition which the surface bonding area is decreased by a surface uneven process such as embossing, a pleats and a crater shaped. Further a sheet-shaped composition having an expand efficiency or an elasticity in a lateral direction is preferable.

A natural fiber such as a cotton, a silk or a linen, a regenerated fiber such as a regenerated cellulose fiber, rayon, copper ammonia rayon and the like, a synthetic fiber such as polyolefin type fiber, polyester type fiber, polyamide type fiber (nylon and the like), polyvinyl alcoholic type fiber, polyacrylonitrile type fiber, polyurethane and the like are eligible for a mini sheet piece.

Particularly in the case of composing the mini sheet piece by a non-woven fabric, a web forming may be any of methods such as a dry method (card method, spun bond method, melt blown method, air laid method) and a wetting method, or a combination of a plurality of methods. Further a bonding method is a thermal bonding, a needle punch method and not limited particularly, and spun lace formed by water confounding method is adequately eligible.

In the case of the mini sheet piece composed by a plastic sheet, a sheet of the thermoplastic resin (PE, PP, PET, poly lactic acid and polybutylene succinate and the like) and porous foaming sheet and the like are eligible. For a method of providing an expanding efficiency and a elasticity to the lateral direction, a method of composing the mini sheet piece by a fiber sheet and a film sheet in which a thermoplastic elastomer resin is used, or a method of composing it by a combination of anti-elastic expanding material and an elastic expanding material such as a thermoplastic elastomer and a natural rubber and the like are eligible.

Figure 16:
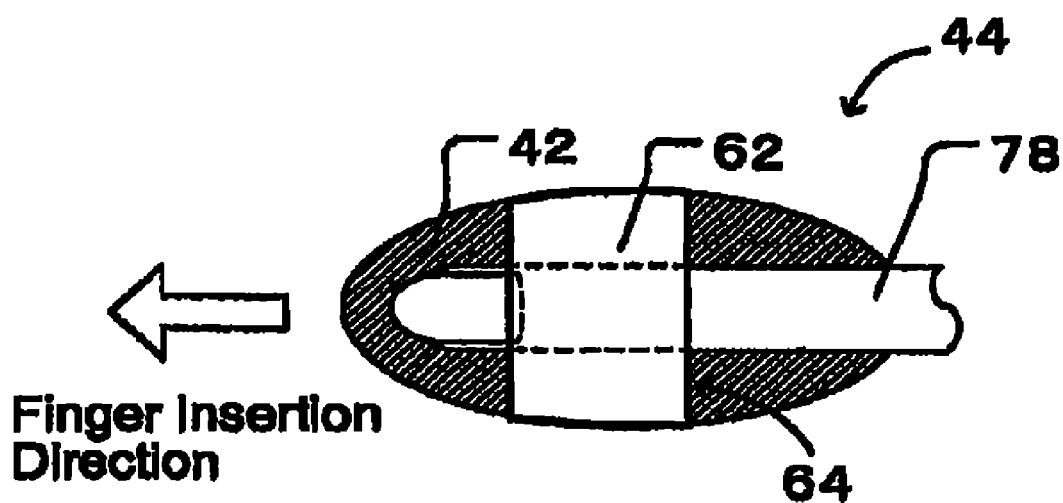
FIG. 16 is a top view of an embodiment of a mini sheet piece of the interlabial pad according to the present invention.

With respect to the form of the mini sheet piece, for example, as shown in FIG. 16, it is eligible to form that along the garment face side of the support sheet 42 comprising the interlabial pad 44, the strip-shaped mini sheet piece 62 is horizontally disposed in the lateral direction of the interlabial pad 44. In this example, the mini sheet piece 62 is fixed at both side ends of the interlabial pad 44 and the opening through 64, that is the finger insertion opening, is formed toward the longitudinal direction of the interlabial pad 44.

Figure 17:
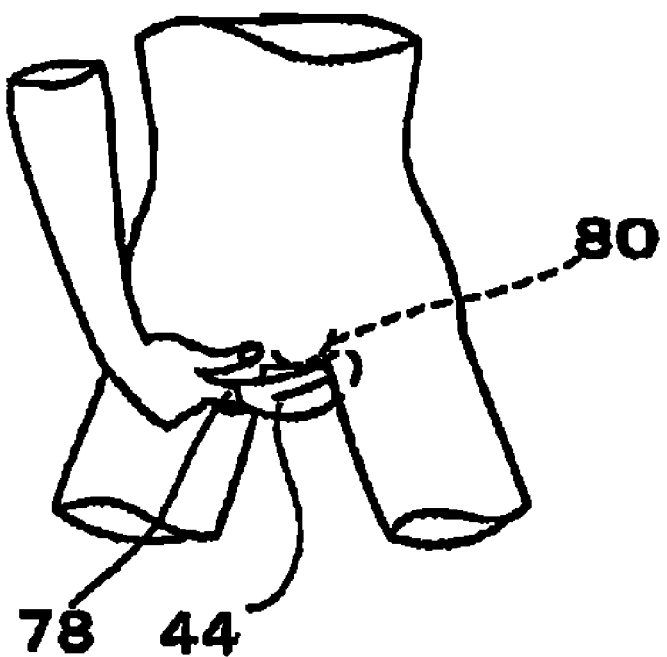
FIG. 17 is an explanation view of a way of wearing the interlabial pad according to the present invention.

In the embodiment, when the finger 78 is inserted into the opening through 64 with contacting a ball of a finger 78 to the support sheet 42, as illustrated in FIG. 17, the longitudinal direction of the interlabial pad 44 and a direction of pudendal slit 80, face in the same direction. Therefore, the interlabial pad 44 can be pushed into the inside of the labia by a ball of the finger 78 so as to attach the interlabial pad 44 certainly.

Figure 18:
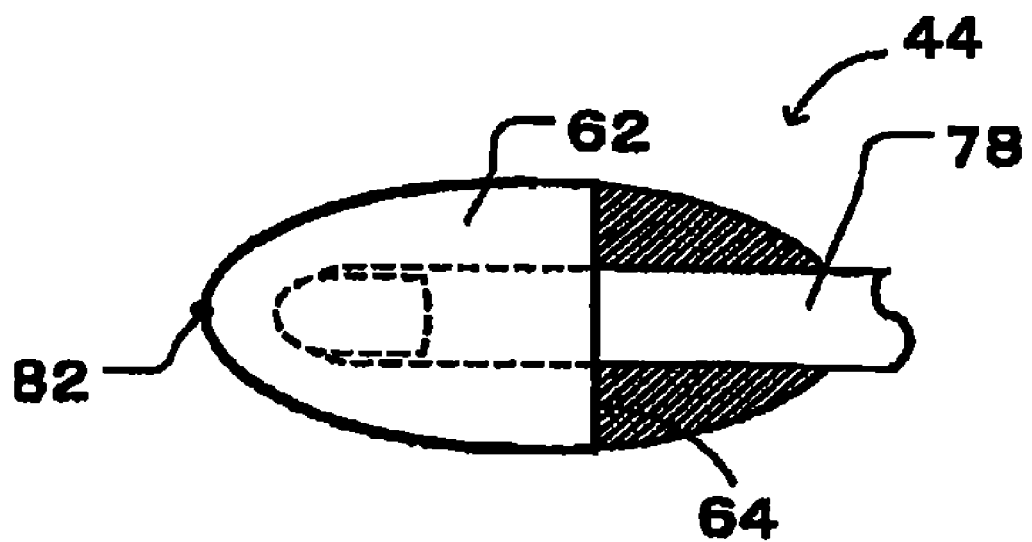
FIG. 18 is a top view of an embodiment of a mini sheet piece of the interlabial pad according to the present invention.

Further the mini sheet piece may be formed as illustrated in FIG. 18, that the support sheet 42 which comprises the interlabial pad 44, is completely covered from the near central portion in the longitudinal direction to an edge end 82 in the longitudinal direction of the interlabial pad 44. The embodiment described hereinbefore is preferable for a sanitary handling of the pad so that the end of the finger 78 is prevented from exposing out of the mini sheet piece 62 and non-contact condition of the menstrual blood and the finger 78 can be maintained.

Figure 19:
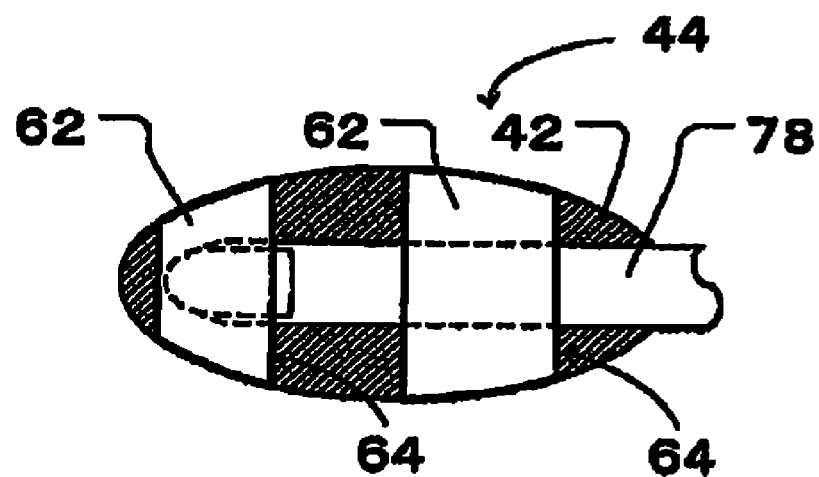
FIG. 19 is a top view of an embodiment of a mini sheet piece of the interlabial pad according to the present invention.

For example, as illustrated in FIG. 19, the end of the finger 91 is also prevented from exposing out of the mini sheet piece 52 by the interlabial pad 44 which a plurality of strip-shaped mini sheet pieces 52 are formed at distance, thereby the effect of the sanitary handling can be achieved as same as the interlabial pad 44 as shown in FIG. 18.

For bonding between the mini sheet piece and the support sheet with an adequate strength, in respect of the bonding strength, it is preferably to set the breaking strength in a lateral direction of the pad in a range from 0.3 to 1.2 N/10 mm. This breaking strength is a strength per a width of 10 mm and a value which is evaluated by a tensilon testing that the mini sheet piece held on the upper chuck and the support sheet held on the lower chuck with a chuck distance of 20 mm, are pulled by a velocity of 100 mm/min.

To achieve an easy identification of the mini sheet piece by the user, the mini sheet piece can be adjusted to have a different color or design, chromaticity from the support sheet by coloring or printing patterns.

[Adhered Portion]

For further decreasing the chance of dropping off the pad from the labia, preferably the adhered portion is formed by coating the adhesive on absorbent body for contacting ostium vaginae, absorbent body for contacting the inner wall of the labia, or the surface of the cover sheet to cover them. This adhered portion is adhered around the labia of the user to decrease the chance of dropping off the pad.

A dot type, a mesh type, a stripe type and the like are eligible for a way of arranging the adhered portion. The position of the adhered portion is not limited particularly, preferably is the place where the pad can be fixed with the body, in consideration of the neighborhood of the labia, particularly the presence of the pubic hair in front of the labia, more preferably to arrange it in a stripe type with a width from 1 to 5 mm or the like near to both sides of the pad.

"Adhered portion" can be formed by coating the adhesive on the surface side sheet. A gel adhesive comprising of a water-soluble polymer, a crosslinking agent, a plasticizer and water are eligible for the adhesive. More concretely, for example of the water soluble polymer, a gelatin, sodium polyacrylate, polyvinyl alcohol, carboxymethylcellulose and the like, for example of crosslinking agent, calcium chloride, a water soluble metallic salt such as magnesium sulfate, for example of a plasticizer, glycerin, wax, paraffin and the like, are eligible.

Other than the above, the pressure sensitive hot melt adhesive can be used for forming the adhered portion. A pressure sensitive adhesive is made up mainly of a syhthetic rubber such as styrene-isoprene-styrene block copolymer (SIS), styrene-butadiene-styrene block copolymer (SBS), styrene-ethylene-butadiene-styrene block copolymer (SEBS), styrene-ethylene-propylene-styrene block copolymer (SEPS) and can be obtained by melting and blending a tackifier such as a terpene resin, a rosin resin and a plasticizer such as a wax and the like.

Further a silicone resin type adhesive can be used. The silicone resin type adhesive is made up mainly of a silicone resin and a fluorine resin and is a compound by blending a crosslinking agent of a metallic salt and the like such as a platinum, molybdenum, antimony and the like and a plasticizer such as ester type wax, glycerin, machine oil and the like.

As described hereinbefore, there are many kinds of adhesives to form the adhered portion, in consideration of the stable coating, it is preferable to use the pressure sensitive hot melt adhesive. For the pressure sensitive hot melt adhesive having a high coating stability, the compound by melting and blending SEBS in the amount from 15 to 25% by mass, the plasticizer in the amount from 15 to 35% by mass and the tackifier in the amount from 40 to 70% by mass is eligible. This pressure sensitive hot melt adhesive may be added an antioxidant or an antifluorescent in the amount from 0.1 to 1.0% by mass.

The example of the evaluation for the adhesive efficiency will be described herein below. In the evaluation, the peel strength of the adhesive (FIG. 20) and the shear strength of the adhesive (FIG. 21) are measured by using a constant speed extending and tensioning tester and a stainless plate 84 having a length of 80 mm×50 mm. In an evaluation test, preliminarily a polyethylene film 86 having substantially the same size of the stainless plate 84 is coated by the adhesive 88 to have a width of 25 mm and a length of 50 mm and are left under the room temperature (20° C.) during thirty minutes. The polyethylene film 86 is laminated and loaded lightly on the stainless plate 84 to contact the adhesive 88 with the plate 84, thereafter is pressed once (one way) by a pressure force of 30 g/cm$^2$ of the roller. Then the plate is left under the room temperature (20° C.) during thirty minutes to obtain a test piece.

Figure 20:
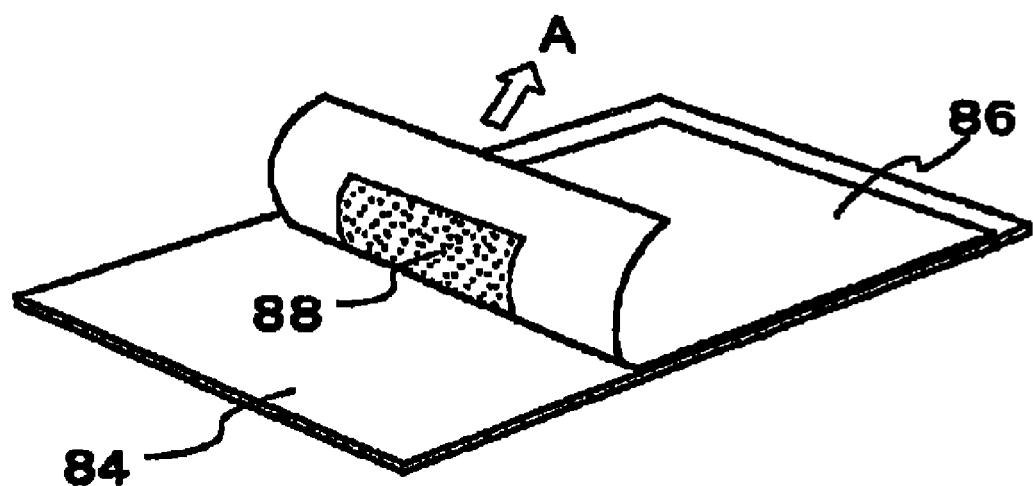
FIG. 20 is an explanation view of experimental condition of a peel strength measurement of the adhesive.
Figure 21:
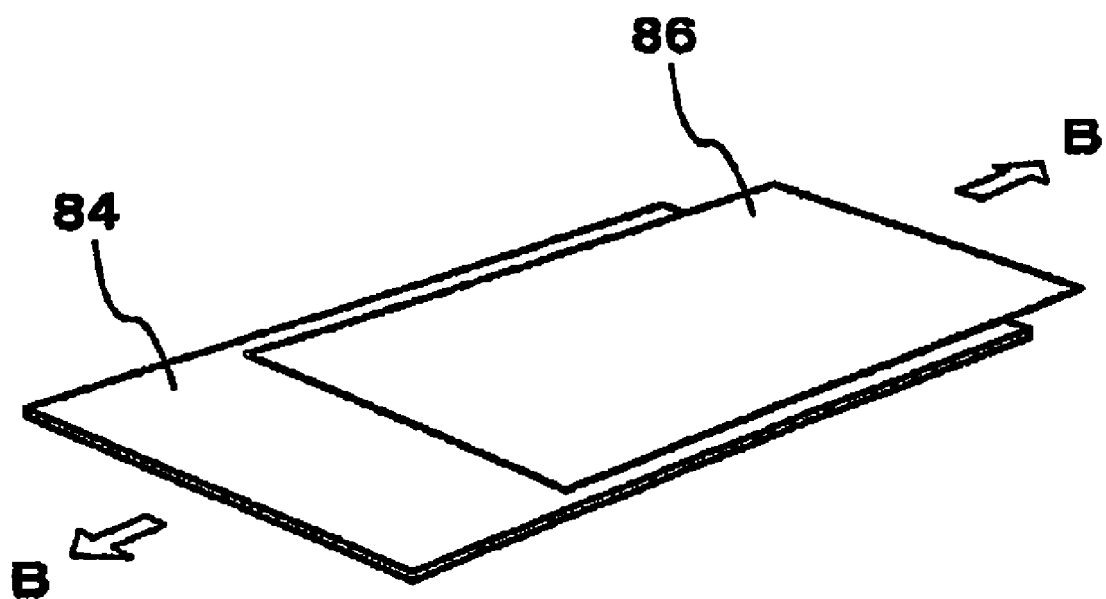
FIG. 21 is an explanation view of experimental condition of a shear strength measurement of the adhesive.

The polyethylene film 86 portion of the obtained test piece is extended to a direction of the arrow A as shown in FIG. 20 and is peeled (180° peeling) in the peel strength test, and is extended to a direction of the arrow B as shown in FIG. 21 in a shear strength test. However, the piece is extended by a test condition of the extending speed of 100 mm/min.

Preferably in the case of the measurement described hereinbefore, a measured value of the peel strength is from 100 to 200 mN/25 mm, and a value of the shear strength is from 3000 to 15000 mN/25 mm in consideration of a burden on a skin of the user.

Furthermore preferably the adhered portion is coated by a sheet comprised of a tissue paper generally used for a separate paper on which silicone resin is coated and by a sheet comprised of a plastic film on which silicone resin is coated. Thereby damage and a separation of the adhered portion during the pads being stored can be prevented.

[Wrapping Container]

The conventional wrapping container can be used for wrapping the interlabial pad according to the present invention. For example, non woven fabric comprised of PE, PP, PET and the like, a film having a thickness from 15 to 60 μm, a paper or laminate materials treated by a lamination of these materials is eligible.

In consideration of a soft feeling, the inner side face of the wrapping container is preferably comprised of materials so that is a crepe tissue in a range from 15 to 50/m$^2$ by total mass of composition, wet spun lace non woven fabric in an amount from 15 to 70 g/m$^2$ by total mass of a composition of a cotton and a pulp and including a cotton in an amount of 10% by mass at least, a spun lace non woven fabric in a range from 20 to 70 g/m$^2$ based on the total mass of the composition and including a rayon in an amount of 30% by mass or more, or melt blown non woven fabric comprised of PP in an amount from 20 to 50 g/m$^2$ by total mass of composition. Further it is also preferable to comprise the container by a composed non woven fabric which is comprised a melt blown non woven fabric in a range from 5 to 20 g/m$^2$ by mass is held between the spun bond non woven fabric in an amount from 6 to 10 g/m$^2$ by total mass of composition. While it is preferable to comprise the outer surface side of the wrapping container in consideration of water durable pressure by a film comprising PE in an amount from 10 to 30 g/m$^2$ by total mass of composition or a porous plastic sheet having a rate or hole area from 10 to 30% and in an amount from 15 to 30 g/m$^2$ by total mass of composition.

The inner and outer face side materials of the wrapping container are laminated in unit by a conventional method of a hot melt adhesive, heat embossing or an ultra sonic closely contacting and the like. In this embodiment, it is preferable to cover the hot melt adhesive in a spiral-shaped or a line-shaped with application coverage from 3 to 10 g/m$^2$ and with a rate of applicant area from 5 to 40%. In case of a heat embossing or an ultra sonic closely contacting, the adhesive is applied in a line-shape, a dot-shape or a cross line-shape and the like in a closely contacting area from 5 to 20% in consideration of the feeling of the laminate material.

[(B) Structure of the Interlabial Pad Provided with Biodegradability, Water Dispersibility and Water Solubility]

Preferably the interlabial pad is comprised of a material of biodegradable rate and/or a material of water dispersible and/or a material of water-soluble. After using the pad comprised of these materials, it can be disposed into a toilet to flush, thereby the destruction of the pad can be easily and sanitarily achieved and the garbage in a toilet can be decreased.

In this Specification, "biodegradable" means that a substance is decomposed by carbon dioxide or a gas such as methane, water and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersible" has the same meaning as water soluble. It means a characteristic in which, while having no influence when used in a limited amount of moisture (menstrual blood), in a large amount of water or water current, the fabric is easily dispersed into small pieces at least to a degree where an ordinal toilet plumbing is not clogged. "Water soluble" is a characteristic in which, while having no influence when used in a limited amount of moisture (menstrual blood), the fabric is soluble in a large amount of water or water current.

[Cover Sheet]

In respect of materials for the cover sheet to have biodegradability, water dispersibility and water solubility, a spun lace non-woven fabric can be used, preferably to use a wetting-shaped spun lace non-woven fabric having a fiber length in a range from 1 to 15 mm. For other materials, a so-called biodegradable resin is used such as a poly lactic acid, polybutylene succinate and the like, for example a melt blown non-woven fabric adjusted the amount from 20 to 60 g/m$^2$ in specific per unit area of the compound which is manufactured by a material of poly lactic acid, a spun bond non-woven fabric adjusted the amount from 15 to 30 g/m$^2$ and a fineness in a range from 1.0 to 3.0 dtex are adequately eligible. Further a single or a continuous fiber of acetate, rayon, synthetic fiber are eligible for other materials so that so-called tow is adjusted in a range of the amount from 10 to 80 g/m$^2$ in specific per unit area of the composition to open each fiber.

[Absorbent Body]

Same materials having water permeability for the cover sheet can be used for materials of the absorbent body to have biodegradability, water dispersibility and water-solubility. Further it is possible to independently use the absorbent body such as sodium alginate, starch, carboxymethylcelluloce and the like, particle-shaped or fiber-shaped super absorbent polymer, or to use a form by mixing these materials with same materials for the cover sheet, In respect of the structure of the absorbent body, the wood pulp and the like are eligible, that is laminated to the amount from 150 to 500 g/m$^2$ by mass to enclose into tissue and is adjusted the thickness from 2 to 10 mm by a press device. It is possible to improve the absorption capacity or keeping ability of the menstrual blood by mixing absorbent body such as starch and the like in a ratio from 5 to 30 g/m$^2$.

[Support Sheet]

In respect of materials for the support sheet to apply biodegradability, water dispersibility and water solubility, and for a water-impermeable support sheet, polyvinyl alcohol film (PVA), a film sheet which one surface or whole or a part of both surfaces are provided with a water proof treatment, PVA film mixed with a silicone resin, a starch film, a sheet laminated of a film which material is a biodegradable resin such as a poly lactic acid or poly butyl succinate and the like and a tissue and the like are eligible. These sheets may be colored by mixing an inorganic pigment in a range from 0.1 to 5% if necessary.

In respect of the embodied structure of non-water permeability support sheet, for example, a laminate paper is formed by a laminating treatment that a film and tissue are bonded. The film comprises poly lactic acid and tissue has a thickness from 10 to 20 μm, in the amount from 15 to 20 g/m$^2$ by mass based on the total mass of composition, are laminated in area ratio from 5 to 40%. The laminate paper described hereinbefore can keep non-water permeability during the pad is wet and it is preferable in preventing the digestion tank from an exceed damage.

[Mini Sheet Piece]

In respect of materials for the mini sheet piece to apply biodegradability, water dispersibility and water solubility, poly lactic acid, polybutylene succinate, a film comprised from PVA and the like, or materials laminated the film of these materials with tissue are eligible.

[Elastic Recovery Member]

In respect of materials for the elastic recovery member to have biodegradability, water dispersibility and water solubility, a natural rubber (cis-1,4-polyisoprene) is eligible.

[Wrapping Container]

For applying biodegradability, water dispersibility and water solubility, the container may be comprised of a fiber sheet using water soluble fiber, a film using biodegradable rate resin or water soluble resin, or a laminated materials of the fiber sheet with the film, a laminated materials of the film and tissue.

[Bonding Method]

Further for a bonding method of applying biodegradability, water dispersibility, water solubility, a bonding method such as adhesion by polyvinyl alcohol and the like having water soluble or water swelling, a heat closely contacting, or a bonding by a hydrogen bonding, and the like can be used individually or can be used in a combination of them adequately.

INDUSTRIAL APPLICABILITY

As described hereinbefore, in the present invention, the absorbing sheet portion includes absorbent body for contacting ostium vaginae which is a stick-shaped or a strip-shaped individual absorbent body to contact with the neighborhood of ostium vaginae of the user, a inner wall of the labia contacting absorbent body which is a flat-shaped individual absorbent body to contact with at least the inner wall of the labia of the user, the absorbent body for contacting ostium vaginae is disposed along the substantial center line of the body face side of absorbent body for contacting the inner wall of the labia, thereby a sealing efficiency with the labia deepest portion comes better in a time of the user moving, a chance of an occurrence of the so-called leak of the menstrual blood and falling of the pad can be prevented.

What is claimed is:

1. An interlabial pad comprising:
 a first absorbent body having a flat shape;
 a second absorbent body provided along a center line in a longitudinal direction of the first absorbent body, the second absorbent body having a stick shape or a strip shape in the longitudinal direction and having an oval cross-sectional shape;

a water permeable cover sheet member covering each of the first absorbent body and the second absorbent body; and a water impermeable support sheet backing the first absorbent body and bonded at peripheral regions of the support sheet to the cover sheet member, wherein the first absorbent body and the second absorbent body are independent, the water permeable cover sheet member includes a first independent cover sheet covering the first absorbent body and a second independent cover sheet covering the second absorbent body, both end portions of the second independent cover sheet in the longitudinal direction connect with both ends of the first independent cover sheet in the longitudinal direction and a central portion of the second independent cover sheet in the longitudinal direction is not bonded to the first independent cover sheet, thereby preventing transmission of movement between the first absorbent body and the second absorbent body, and an elastic recovery member is embedded in an interior of the second absorbent body disposed between both end portions of the second independent cover sheet in the longitudinal direction, and a width of the elastic recovery member in a cross section when unloading is in a range from 1 to 10 mm.

2. The interlabial pad according to claim 1, wherein a length of the interlabial pad in the longitudinal direction is 50 to 150 mm, the first absorbent body has a width in a lateral direction of 10 to 60 mm and the second absorbent body has a width in the lateral direction of 1.5 to 40 mm.

3. The interlabial pad according to claim 1, wherein the elastic recovery member includes an elastomer compound in an amount from 10 to 90% by mass.

4. The interlabial pad according to claim 1, wherein the elastic recovery member includes an elastomer compound in an amount from 15 to 60% by mass.

5. The interlabial pad according to claim 1, further comprising a mini sheet piece bonded on a garment side of the support sheet, the mini sheet piece having one or more bonding portions at each side portion in the longitudinal direction of the support sheet, and having one or more non-bonding portion in the lateral direction of the support sheet, wherein between the mini sheet piece and the support sheet, at least one of said one or more non-bonding portion forms a finger insertion opening.

6. The interlabial pad according to claim 1, wherein the interlabial pad is used together with a sanitary napkin.

7. The interlabial pad according to claim 1, wherein the interlabial pad is a pad for incontinence of urine.

8. The interlabial pad according to claim 1, wherein the interlabial pad is a pad for absorbing vaginal discharge.

9. A wrapping body, wherein the interlabial pad according to claim 5 is contained in a wrapping container for individually wrapping the interlabial pad.

10. A wrapping body, wherein the interlabial pad according to claim 5 is contained in a wrapping container for individually wrapping the interlabial pad, the wrapping container having a break seal opening and the interlabial pad being positioned in the wrapping container so that the finger insertion opening faces toward the break seal opening of the wrapping container.

11. The wrapping body according to claim 10, wherein the interlabial pad is positioned in the wrapping container such that the mini sheet piece is formed in a mountain-folded shape toward the garment side direction substantially along the center line in the longitudinal direction of the interlabial pad.

12. The interlabial pad of claim 1, wherein the elastic recovery member has an elliptical shape.

* * * * *